US008889737B2

(12) United States Patent
Cuevas Sànchez et al.

(10) Patent No.: US 8,889,737 B2
(45) Date of Patent: *Nov. 18, 2014

(54) USE OF 2,5-DIHYDROXYBENZENE COMPOUNDS AND DERIVATIVES FOR THE TREATMENT OF SKIN CANCER

(75) Inventors: Pedro Cuevas Sànchez, Madrid (ES); Guillermo Gimenez Gallego, Madrid (ES); Inigo Saenz de Tejada Morgan, Madrid (ES); Javier Angulo Frutos, Valdemoro (ES); Serafin Valverde Lopez, Madrid (ES); Antonio Romero Garrido, Madrid (ES); Rosa Maria Lozano Puerto, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/326,778

(22) Filed: Dec. 15, 2011

(65) Prior Publication Data
US 2012/0087904 A1 Apr. 12, 2012

Related U.S. Application Data

(63) Continuation of application No. 11/839,522, filed on Aug. 15, 2007, now Pat. No. 8,101,660.

(30) Foreign Application Priority Data

Jul. 2, 2007 (ES) .................................. 200701856
Aug. 16, 2007 (ES) .................................. 200602218

(51) Int. Cl.
*A61K 31/222* (2006.01)
(52) U.S. Cl.
USPC .......................................... 514/546; 514/576
(58) Field of Classification Search
None
See application file for complete search history.

(56) References Cited

U.S. PATENT DOCUMENTS

| | | | |
|---|---|---|---|
| 4,115,648 A | 9/1978 | Esteve-Subirana | |
| 4,837,378 A | 6/1989 | Borgman | |
| 4,970,202 A | 11/1990 | Trigger | |
| 5,519,018 A | 5/1996 | Matusch et al. | |
| 5,698,595 A | 12/1997 | Boelle et al. | |
| 6,281,203 B1 | 8/2001 | Touzan et al. | |
| 6,664,406 B1 | 12/2003 | Coupland et al. | |
| 6,787,573 B2 | 9/2004 | Nottet | |
| 8,101,660 B2 * | 1/2012 | Sanchez et al. | 514/546 |
| 2002/0143052 A1 | 10/2002 | Lan-Hargest et al. | |
| 2003/0216418 A1 | 11/2003 | Stogniew et al. | |
| 2004/0167222 A1 | 8/2004 | Brooks et al. | |
| 2005/0175559 A1 | 8/2005 | DiNardo et al. | |
| 2006/0258730 A1 | 11/2006 | Allegretti et al. | |
| 2007/0032471 A1 | 2/2007 | Torrens Jover et al. | |
| 2007/0149618 A1 | 6/2007 | Cuevas Sanchez et al. | |
| 2008/0114060 A1 | 5/2008 | Cuevas Sanchez et al. | |
| 2008/0114075 A1 | 5/2008 | Cuevas Sanchez et al. | |
| 2009/0111779 A1 | 4/2009 | Cuevas Sanchez et al. | |

FOREIGN PATENT DOCUMENTS

| | | |
|---|---|---|
| EP | 0204987 | 5/1986 |
| EP | 1719509 | 11/2006 |
| WO | WO-96/17589 | 6/1996 |
| WO | WO-96/25159 | 8/1996 |
| WO | WO-2005/013962 | 2/2005 |
| WO | WO-2005/077352 | 8/2005 |
| WO | WO-2006/029484 | 3/2006 |
| WO | WO-2006/069806 | 7/2006 |

OTHER PUBLICATIONS

"Actinic Keratosis and Other Precancers", http//www.skincancer.org 2008 , 3 pgs.
"Catalogo de especialidades farmaceuticas 1991", *Consejo General De Colegios Oficiales De Farmaceuticos* 1991 , 4 pgs.(w/ summary in English).
"Causes of Barrett's Esophagus", http://digestive-system.emedtv.com/barrett's-esophagus/causes-of-barrett's-esophagus.html Nov. 2006 , 3 pgs.
"Crohn's Disease", http://cholitis.emedtv.com/crohn'sdisease/crohn's-disease-causes.html 2008 , 3 pgs.
"Definition of Rosacea", American Heritage Medical Dictionary, www.freedictionary 2007 , 6 pgs.
"English translation of Acnisdin and Acnisdin Retinoico entries in Catalogo de especialidades farmaceuticas", *Consejo General de Colegios Oficiales De Farmaceuticos* 1991 , 2 pgs.
"Final Office Action in U.S. Appl. No. 11/839,515", mailed on May 5, 2010 , 11 pages.
"Final Office Action in U.S. Appl. No. 11/839,520", mailed on May 21, 2010 , 10 pages.
"International Search Report of PCT/EP2007/058439", mailed on Nov. 28, 2007 , 4 pages.
"International Search Report of PCT/EP2007/058438", mailed on Nov. 27, 2007 , 4 pages.
"International Search Report of PCT/EP2007/058440", mailed on Feb. 22, 2008 , 5 pages.
"International Search Report of PCT/EP2007/058441", mailed on Nov. 14, 2007 , 4 pages.
"International Search Report of PCT/EP2007/058443", mailed on Nov. 9, 2007 , 3 pages.
"International Search Report of PCT/EP2007/058444", mailed on Nov. 28, 2007 , 4 pages.
"International Search Report of PCT/EP2007/058445", mailed on Nov. 26, 2007 , 4 pages.
"International Search Report of PCT/EP2007/058446", mailed on Nov. 30, 2007 , 4 pages.
"International Search Report of PCT/EP2007/058447", mailed on Dec. 3, 2007 , 4 pages.

(Continued)

*Primary Examiner* — James D Anderson
(74) *Attorney, Agent, or Firm* — Servilla Whitney LLC

(57) ABSTRACT

The present invention relates to the use of a 2,5-dihydroxybenzene derivative of formula (I) or a pharmaceutically acceptable salt, solvate, isomer, or prodrug thereof for the treatment and/or prophylaxis of, inter alia, skin cancer.

15 Claims, 15 Drawing Sheets

(56) References Cited

OTHER PUBLICATIONS

"International Search Report of PCT/EP2007/058451", mailed on Nov. 30, 2007, 4 pages.
"International Search Report of PCT/EP2007/058453", mailed on Jul. 15, 2008, 6 pages.
"International Search Report of PCT/EP2007/058454", mailed on Feb. 19, 2008, 4 pages.
"International Search Report of PCT/EP2007/058456", mailed on Dec. 6, 2007, 7 pages.
"International Search Report of PCT/ES2005/070017", mailed on Jun. 22, 2005, 2 pages.
"Remington's Pharmaceutical Sciences", 1980, 7 pgs.
"Reply to Written Opinion in Internation Application PCT/EP2007/058440", mailed on Jul. 17, 2008, 30 pages.
"Written Opinion of PCT/EP2007/058438", mailed on Nov. 27, 2007, 7 pages.
"Written Opinion of PCT/EP2007/058440", mailed on Feb. 22, 2008, 8 pages.
"Written Opinion of PCT/ES2005/070017", mailed on Jun. 22, 2005, 3 pages.
Angulo, Javier et al., "Calcium dobesilate potentiates endothelium-derived hyperpolarizing factor-mediated relaxation of human penile resistance arteries", *British Journal of Pharmacology* 000 2003, 1-9.
Arhanic, V. et al., "Attempts at Treating Bureosis with Angioprotective Agents", *Annals of the Dr. M. Stojanovic Hospital*, vol. 15:120 1976, 9 pgs.
Arican, Ozer et al., "Serum Levels of TNF-a, IFN-y, IL-6, 1L-8, 1L-12, 1L-17, and IL-18 in Patients With Active Psoriasis and Correlation With Disease Severity", *Mediators of Inflamation*, vol. 5 2005, pp. 273-279.
Banarroch, Isaac S. et al., "Treatment of Blook Hyperviscosity with Calcium Dobesilate in Patients with Diabetic Retinopathy", *Ophthalmic Res.* 17 1985, 131-138.
Banker, Gilbert S. et al., *Modern Pharmaceutics, 3rd Edition* Marcel Dekker, Inc. 1996, 451 & 596.
Benakis, A. et al., "Localisation, distribution, eliination et metabolisme du dihydroxy-2,5, benzene sulfonate de Ca (Dobesilate de Ca) marque par le S35 chez la souris, le rat et le lapin", *Congres International de Therapeutique* 1974, 16 pgs.
Bonifati, C. et al., "Correlated increases of tumour necrosis factor-a, interleukin-6 and granulocyte monocyte-colony stimulating factor levels in suction blister fluids and sera of psoriatic patients-relationships with disease severity", *Clinical and Experimental Dermotology*, vol. 19 1994, pp. 383-387.
Brannon, Heather, "Atopic Dermatitis Treatment: Medications and Measures that can Improve Symptoms of Atopic Dematitis", http://dermatology.about.com/csjeczemadermatitis/a/atopictx.htm 2005, 2 pages.
Braverman Im, Sibley J. et al., "Role of the microcirculation in the treatment and pathogenesis of psoriasis.", *J. Invest. Dermatol.*, vol. 78 1982, pp. 12-17.
Brunet, J. et al., "In vitro antioxidant properties of calcium dobesilate", *Fundam Clin Pharmacol* 12 1998, 205-212.
Castells-Rodellas, A. et al., "Interleukin-6 in Normal Skin and Psoriasis", *Acta Derm Venereol (Stockh)*, vol. 72 1992, pp. 165-168.
Cho, Jae-We et al., "Curcumin attenuates the expression of IL-18, IL-6, and TNF-a as well as cyclin E in TNF-a-treated HaC aT cells; NF-KB and MAPKs as potential upstream targets", *International Journal of Molecular Medicine*, vol. 19 2007, pp. 469-474.
Creamer, D. et al., "Angiogenesis in psoriasis", *Angiogenesis*, vol. 5 2002, pp. 231-236.
Cuevas, Pedro et al., "Dobesilate in the Treatment of Plaque Psoriasis", *Eur J Med Res* 10 2005, 373-376.
Cuevas, P. et al., "Treatment of basal cell carcinoma with dobesilate", *Am Acad Dermatol* 2005, 526-527.
Divers, A.K. et al., "Keratoacanthoma centrifugum marginatum: a diagnostic and therapeutic challenge", *Curtis*, vol. 73, No. 4 2004, 257-262.
Dormond, Olivier et al., "Inhibitor of tumor angiogenesis by non-steroidal anti-inflammatory drugs: emerging mechanisms and therapeutic perspectives", *Drug Resistance Updates* 4 2002, 314-321.
Dorwald, F. Zaragoza, "Side Reactions in Organic Synthesis. A Guide to Sucessful Synthesis Design", *Wiley-VCH Verlag GmbH & Co.* 2005, 4 pgs.
Gambichler, T. et al., "Cytokine mRNA expression in basal cell carcinoma", *Arch Dermatol Res* 298 2006, 139-141.
Goldman, Lee et al., "Principles of Cancer Therapy", *Cecil Textbook of Medicine*, vol. 1, W.B. Saunders Company 2000, 1060-1074.
Graber, R. et al., "Calcium Dobesilate protects human peripheral blood mononuclear cells from oxidation and apoptosis", *Apoptosis* 3 1998, 41-49.
Griffioen, Arjan W. et al., "Angiogenesis: Potentials for Pharmacologic Intervention in the Treatment of Cancer, Cardiovascular Diseases, and Chronic Inflammation", *Pharmacological Reviews*, vol. 52, No. 2 2000, pp. 237-268.
Gudjonsson, J. E. et al., "Immunopathogenic mechanisms in psoriasis", *Clin. Exp. Immunol.*, vol. 135 2004, pp. 1-8.
Heidenreich, R. et al., "Angiogenesis: the new potential target for the therapy of psoriasis?", *Drug News Perspect*, vol. 21 2008, pp. 97-105 (abstract).
Hodge, David R. et al., "The role of IL-6 and STAT3 in inflammation and cancer", *European Journal of Cancer* 41 2005, 2502-2512.
Hornick, Jason L. et al., "A New Chemically Modified Chimeric TNT-3 Monoclonal Antibody Directed Against DNA for the Radioimmunotherapy of Solid Tumors", *Cancer Biotherapy & Radiopharmaceuticals*, vol. 13, No. 4 1998, 255-268.
Jee, Shiou-Hwa et al., "Interleukin-6 Induced Basic Fibroblast Growth Factor-Dependent Angiogenesis in Basal Cell Carcinoma Cell Line via JAK/STAT3 and PI3-Kinase/Akt Pathways", *J Invest Dermatology* 123 2004, 1169-1175.
Jee, Shiou-Hwa et al., "Overexpression of interleukin-6 in human basal cell carcinoma cell lines increases anti-apoptotic activity and tumorigenic potency", *Onogena* 20 2001, 198-208.
Jee, S. H. et al., "The Phosphotidyl Inositol 3-Kinase/Akt Signal Pathway is Involved in Interleukin-6-mediated Mcl-1 Upregulation and Anti-apoptosis Activity in Vasal Cell Carcinoma Cells", *The Journal of Investigative Dermatology*, vol. 119, No. 5 2002, 1121-1127.
Jegasothy, Brian V. et al., "Tacrolimus (FK 506)—A New Therapeutic Agent for Severe Recalcitrant Psoriasis", *Arch Dermatol*, vol. 128 Jun. 1992, 781-785.
Johnson, JL et al., "Relationships between drug activity in NCI preclinical in vitro and in vivo models and early clinical trials", *British Journal of Cancer* 94(10) 2001, 1424-1431.
Jordan, V. C., "Tamoxifen: A Most Unlikely Pioneering Medicine", *Nature Reviews Drug Discovery*, vol. 2 2003, 205-213.
Karasek, Marvin A., "Progress in our understanding of the biology of psoriasis", *Cutis*, vol. 64, Iss. 5 Nov. 1999, 5 pgs.
Kaur, Charandeep et al., "An open trial of calcium dobesilate in patients with venous ulcers and stasis dermatitis", *International Journal of Dermatology* 42 2003, 147-152.
Khawli, Leslie A. et al., "Comparison of Recombinant Derivatives of Chimeric TNT-3 Antibody for the Radioimaging of Solid Tumors", *Hybridoma and Hybridomics*, vol. 22, No. 1 2003, 1-10.
Kocak, MD, Mukadder et al., "Examination of Bcl-2, Bcl-X and bax protein expression in psoriasis", *International Journal of Dermatology* 42 2003, 789-793.
Lameynardie, Stephane et al., "Inhibition of choroidal angiogenesis by calcium dobesilate in normal Wistar and disbetic GK rats", *European Journal of Pharmacology* 510 2005, 149-156.
Leman, J. A. et al., "Treatment of severe psorasis with infliximab", *Ther. Clin. Risk Manag.*, vol. 4 2008, pp. 1165-1176.
Lens, M. et al., "Current clinical overview of cutaneous melanoma", *British Journal of Nursing*, vol. 17, No. 5 2008, 2 pgs.
Losa, Gabriele A. et al., "Preventionof Oxidation and Apoptosis in Human Peripheral Blood Mononuclear Cells Exposed to Caldium Dobesilate", *International Journal of Angiology* 8 1999, 511-515.
Lozano, Rosa M. et al., "Solution Structure of Acidic Fibroblast Growth Factor Bound to 1,3,6-Naphthalenetrisulfonate: A Minimal Model for the Anti-tumoral Actionof Suramins and Suradistas", *J. Mol. Biol.* 281 1998, 899-915.

(56) References Cited

OTHER PUBLICATIONS

Mee, John B. et al., "Interleukin-1: A key inflammatory mediator in psoriasis?", *Cytokine*, vol. 33 2006, pp. 72-78.

Michal, M. et al., "Effect of Calcium Dobesilate on Platelet Function", *Thrombosis Research* 51 1988, 593-605.

Mossner, Rotraut et al., "Tumor necrosis factor antagonists in the therapy of psoriasis", *Clinics in Dermatology*, vol. 26 2008, pp. 486-502.

Newell, B. et al., "Comparison of the microvasculature of basal cell carcinoma and actinic keratosis using intravital microscopy and immunohistochemistry", *British Journal of Dermatology* 149 2003, 105-110.

Nickoloff, Brian J., "Characterization of Lymphocyte-Dependent Angiogenesis Using a SCID Mouse: Human Skin Model of Psoriasis", *J. Investig. Damatol. Symp. Proc.*, vol. 5 2000, pp. 67-73.

Nickoloff, Brian J. et al., "Recent insights into the immunopathogenesis of psoriasis provide new therapeutic opportunities", *J. Clin. Invest.*, vol. 113 2004, pp. 1664-1675.

Niwa, Y. et al., "Topical applicationof the immunosuppressant tacrolimus accelerates carcinogenesis in mouse skin", *British Journal of Dermatology* 149 2003, 960-067.

Nour, A. F. et al., "Preliminary Clinical Study with Calcium Dobesilate in Fibrocystic Disease of the Breast", *Acta Therapeutica*, vol. 12. No. 3 1986, 233-241.

O'Grady, Anthony et al., "COX-2 Expression Correlates With Microvessel Density in Non-Melanoma Skin Cancer From Renal Transplant Recipients and Immunocompetent Individuals", *Human Pathology*, vol. 35, No. 12 2004, 1549-1555.

Oh, Chang-Keun et al., "Expression of Basic Fibroblast Growth Factor, Vascular Endothelial Growth Factor, and Thrombospondin-1 Related to Microvessel Density in Nonaggressive and Aggressive Basal Cell Carcinomas", *The Journal of Dermatology*, Vo. 30 2003, 306-313.

Ruiz, Emilio et al., "Calcium Dobesilate Increases Endothelium-Dependent Relaxation in Endothelium-Injured Rabbit Aorta", *Pharmacological Research*, vol. 38, No. 5 1998, 361-366.

Rutkowski, Suzanne, "Mystified by Your Medications?", *Asthma Magazine* 2001, 9-12.

Sabat, Robert et al., "Immunopathogenesis of psoriasis", *Exp. Dermatol.*, vol. 16 2007, pp. 779-798.

Sausville, Edward A. et al., "Contributions of Human Tumor Xenografts to Anticancer Drug Development", *Cancer Res* 66(7) Apr. 1, 2006, 3351-3354.

Schon, MD, Michael et al., "Psoriasis", *The New England Journal of Medicine* 2005, 1899-1912.

Schulze, H. J. et al., "Imiquimod 5% cream for the treatment of superficial basal cell carcinoma: results from a randomized vehicle-controlled phase III study in Europe", *British Journal of Dermatology* 152 2005, 939-947.

Sintov, Amnon C. et al., "Percutaneous penetration and skin metabolism of ethylsalicylate-containing agent, UT-2100: in-vitro and in-vivo evaluation in guinea pigs", *Journal of Controlled Release* 79 2002, 113-122.

Skov, L. et al., "Basal cell carcinoma is associated with high TNF-a release but not with TNF-a polymorphism at position 308", *Experimental Dermatology* 12 2003, 772-776.

Staibano, MD, S. et al., "The Prognostic Significance of Tumor Angiogenesis in Nonaggressive and Aggressive Basal Cell Carcinoma of the Human Skin", *Human Pathology*, vol. 27 No. 7 1996, 695-700.

Stanton, Anthony W. et al., "Expansion of Micorvascular Bed and Increased Solute Flux in Human Basal Cell Carcinoma in Vivo, Measured by Fluorescein Video Angiography", *Cancer Research* 63 2003, 3969-3979.

Stanwell, Caroline et al., "The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition", *Cancer Research*, vol. 55 1995, 4950-4956.

Stockfleth, E. et al., "Successful treatment of actinic keratosis with imiquimod cream 5%: a report of six cases", *British Journal of Dermatology*, 144 2001, 1050-1053.

Suschek, Christoph et al., "Dobesilate enhances endothelial nitric oxide synthase-activity in macro-and microvascular endothelial cells", *British Journal of Pharmacology* 122 1997, 1502-15-8.

Takatsuka, Yoshikazu et al., "Various Analogues to Anthranilic Acid and Their Anti-Cancer Effects", *Mie Medical Journal*, vol. XVII, No. 1 1987, 11 pgs.

Tjiu, Jeng-Wei et al., "Cyclooxygenase-2 Overexpression in Human Basal Cell Carcinoma Cell Line Increases Antiapoptosis, Angiogenesis, and Tumorigenesis", *The Society for Investigative Dermatology* 2006, 1143-1151.

Tjiu, Jeng-Wei et al., "Tumor-Associated macrophage-Induced Invasion and Angiogenesis of Human Basal Cell Carcinoma Cells by Cyclooxygenase-2 Induction", *Journal of Investigative Dermatology* 2009, 1016-1025.

Travis, Lisa et al., "Mdical Backgrounder: Psoriasis", *Drugs of Today*, 38(12) 2002, 847-865.

Trozak, Daniel J., "Topical corticosteriod therapy in psoriasis vulgaris: Update and new strategies", *Cutis.*, vol. 64, Iss. 5 5 pgs., Nov. 1999.

Vippagunta, Sudha R. et al., "Crystalline solids", *Advanced Drug Delivery Reviews* 48 2001, 3-26.

Wolff, Manfred E., "Burger's medicinal Chemistry and Drug Discovery", *Fifth Edition* vol. 1: *Principles and Practice* 1995, 4 pgs.

Wollina, U. et al., "Toxicity of Methotrexate Treatment in Psoriasis and Psoriatic Arthritis—Short and Long-Germ Toxicity in 104 Patients", *Clin Rheumatol* 20 2001, 406-410.

Yamada, Katsuhisa et al., "Inhibitory Effect of Diacetyl Gentisic Acid on Melanogenesis", *Journal of Japanese Cosmetic Science Society*, vol. 22, No. 3 1998, 169-174.

\* cited by examiner carrier (0.9% NaCl)

DHBS (100 mg/kg/day)

DABS (100 mg/kg/day)

USE OF 2,5-DIHYDROXYBENZENE COMPOUNDS AND DERIVATIVES FOR THE TREATMENT OF SKIN CANCER

CROSS-REFERENCE TO RELATED APPLICATIONS

This application is a Continuation of and claims the benefit of priority of pending U.S. application Ser. No. 11/839,522, filed on Aug. 15, 2007, which claims the benefit of priority under 35 U.S.C. §119 of ES Application No. P200602218, filed Aug. 16, 2006 and of ES Application No. P200701856, filed Jul. 2, 2007. The foregoing applications, and all documents cited therein, are hereby incorporated herein by reference in their entirety.

TECHNICAL FIELD

The invention relates to the use of 2,5-dihydroxybenzene derivatives, their pharmaceutically acceptable salts and solvates, as well as isomers and prodrugs thereof for the treatment of hematological dyscrasias, including myelodysplastic syndromes (MDSs); cancer in an organ, particularly skin cancer; and fibrosis, as well as for improving the efficacy of chemotherapy, radiation therapy and/or cancer immunotherapy.

BACKGROUND

In spite of recent advances in chemotherapy and radiation, cancer is one of the main causes of death at any age worldwide. In the United States alone there are almost three million new cancer cases diagnosed every year. The overall five-year survival is close to fifty percent for all patients, and the prognosis is still particularly bad for those patients with advanced solid tumors.

Rosacea is a frequent ocular and facial disease usually affecting millions of people worldwide. It is a chronic and progressive vascular skin disorder, involving mainly the malar and nasal areas of the face. Rosacea is characterized by erythema, papules, pustules, telangiectasia, facial edema, ocular lesions and in its most advanced and severe form, tissue and sebaceous gland hyperplasia leading to rhinophyma. Rhinophyma, a florid overgrowth of the tip of the nose with hypervascularity and nodularity, is an uncommon progression of rosacea with an unknown cause. Ocular lesions, including mild conjunctivitis, burning and gritty sensation, are common. Blepharitis, the most common ocular manifestation, is a non-ulcerative condition of the eyelid margins.

Psoriasis is a chronic disease affecting approximately 2-3% of the world population. It is characterized by epidermal cell hyperproliferation. Psoriasis symptoms include clearly defined erythematous spots covered by a characteristic crust, epidermal hyperproliferation, peeling and incomplete keratinocyte differentiation. Clinical psoriasis variants include erythrodermic, seborrheic, reverse and photosensitive psoriasis and psoriasis guttata, pustular variants and Reiter's disease. There is currently no cure for psoriasis.

There is still a need for new effective therapies for treating cancer and treating fibrosis.

SUMMARY

The inventors have surprisingly found that 2,5-dihydroxybenzene derivatives, their pharmaceutically acceptable salts and solvates, as well as isomers and prodrugs thereof are useful in preparing medicinal products for treating skin cancer.

In certain embodiments, the invention provides a method for the treatment or prophylaxis of skin cancer, comprising administering to a subject in need thereof, an effective amount of a 2,5-dihydroxybenzene derivative represented by Formula (I) or a pharmaceutically acceptable salt, solvate, isomer or prodrug thereof, wherein the compound of Formula (I) is:

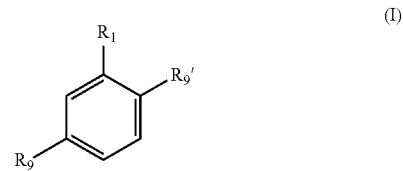

(I)

wherein:

$R_1$ is —$(CH_2)_a Y$ or —$CH=CH$—$(CH_2)_p Z$;

Y is —$SO_3H$, —$SO_3^-.X^+$, —$SO_3R_3$, —$PO_3H$, —$PO_3^-.X^+$, or —$PO_3R_3$, wherein when Y is —$SO_3H$, $SO_3^-.X^+$ or —$SO_3R_3$, then $R_9$ and $R_{9'}$ are independently selected from —OH and —$OR_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group;

Z is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;

$X^+$ is an organic cation or an inorganic cation, such that the general charge of the compound is neutral;

$R^9$ and $R^{9'}$ are independently selected from —OH and —$OR_2$, wherein when $R^9$ and $R^{9'}$ are both —$OR_2$, then said $R_9$ and $R_{9'}$ can be the same or different;

$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;

$R_3$ is a substituted or unsubstituted alkyl group or a substituted or unsubstituted aryl group;

a is a number selected from 0, 1, 2, 3, 4, 5 and 6; and p is an integer selected from 0, 1, 2, 3, 4, 5 and 6.

In certain embodiments, $R_1$ is —$(CH_2)_a Y$ or —$CH=CH$—$(CH_2)_p Y$. In other embodiments, Y is selected from —$SO_3H$, —$SO_3^-.X^+$, —$SO_3R_3$. In yet other embodiments, $R_3$ is selected from methyl and ethyl. In some embodiments, $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In some embodiments, $R_2$ is selected from methylcarbonyl, phenylsulfonyl, 4-methylphenylsulfonyl, benzylsulfonyl, benzyl and phenyl.

In certain embodiments, the compound of Formula (I) is selected from the group consisting of: 5-hydroxy-2-{[(4-methylphenyl)sulfonyl]oxy}benzenesulfonic acid; 2-hydroxy-5{[(4-methylphenyl)sulfonyl]oxy}benzenesulfonic acid; 2,5-bis{[(4-methylphenyl)sulfonyl]oxy}benzenesulfonic acid; 2-(acetyloxy)-5-hydroxybenzenesulfonic acid; 5-(acetyloxy)-2-hydroxybenzenesulfonic acid; 2,5-bis(acetyloxy)benzenesulfonic acid; 5-hydroxy-2-{[(4-methylphenyl)sulfonyl]oxy}benzenehomosulfonic acid; 2-hydroxy-5-{[(4-methylphenyl)sulfonyl]oxy}benzenehomosulfonic acid; 2,5-bis{[(4-methylphenyl)sulfonyl]oxy}benzenehomosulfonic acid; 2-(acetyloxy)-5-hydroxybenzenehomosulfonic acid; 5-(acetyloxy)-2-hydroxybenzenehomosulfonic acid; 2,5bis(acetyloxy)benzenehomosulfonic acid; 3-(2,5-dihydroxyphenyl)-2-propenoic acid (2,5-dihydroxycinnamic acid); 3-(5-hydroxy-2-{[(4-methylphenyl)sulfonyl]oxy}phenyl)-2-propenoic acid; 3-(2-hydroxy-5-{[(4-methylphenyl)sulfonyl]oxy}phenyl)-2-propenoic acid; 3-(2,5-bis{[(4-methylphenyl)sulfonyl]oxy}phenyl)-2-propenoic acid; 3-(2-(acetyloxy)-5-hydroxyphenyl)-2propenoic acid; 3-(5-(acetyloxy)-2-hydroxyphenyl)-2-propenoic acid; 3-(2,5bis(acetyloxy)phenyl)-2-propenoic acid; 3-(2-(benzyloxy)-5-hydroxyphenyl)-2-propenoic acid; 3-(5-(benzyloxy)-2-hydroxyphenyl)-2-propenoic acid; 3-(2,5-bis(benzyloxy)phenyl)-2-propenoic acid; and pharmaceutically acceptable salts, solvates, and prodrugs thereof.

In certain embodiments, the compound of Formula I is selected from: 2-(acetyloxy)-5-hydroxybenzenesulfonic acid; 5-(acetyloxy)-2-hydroxy benzene sulfonic acid and 2,5-bis(acetyloxy)benzenesulfonic acid.

In certain embodiments, the invention provides a method for the treatment and/or prophylaxis of skin cancer, wherein the skin cancer is selected from the group consisting of: lentigo maligna, melanoma, keratoacanthoma, basal cell carcinoma (BCC), squamous cell carcinoma (SCC), Merkel cell carcinoma (MCC), sarcoma, angiosarcoma, cutaneous lymphoma, sweat gland carcinoma, and sebaceous gland carcinoma.

Advantageously, a compound of Formula (I) is administered topically. In certain embodiments, the compound of Formula (I) is administered orally, buccally, transdermally, by inhalation, rectally, intravaginally, intraocularly, or otically.

In certain embodiments, the invention provides a method for the treatment and/or prophylaxis of skin cancer, further comprising administration of at least one additional therapeutic agent.

Examples of suitable therapeutic agents include those selected from the group consisting of: imiquimod, diclofenac, glycidic acid, trichloroacetic acid, colchicine, T4 endonuclease, fluorouracil, isotretinoin, acitretin, cidofoir, 5-aminolevulinic acid, methyl aminolevulinate, hypericin, a chemotherapeutic agent, a corticosteroid, an antibiotic, an analgesic, an immunomodulator, an anti-angiogenic, including anti-VEGF, anti-FGF, anti-EGF and anti-HGF and their respective receptors; a leukotriene modifier, an aminosalicylate, an anesthetic, a nonsteroidal anti-inflammatory, a modifier of a solubilized interleukin receptor, a cytotoxic agent, inhibitors of tyrosin-kinase receptors, protein kinase C inhibitors, and a combination of two or more thereof.

In certain embodiments, the invention provides a method for the treatment and/or prophylaxis of skin cancer, further comprising at least one coadjuvant therapy selected from the group consisting of: photodynamic therapy, cryotherapy, curettage and surgery.

In certain embodiments, the invention relates to the administration of a compound of Formula (1), wherein the compound is administered at least once per week. In other embodiments, the compound is administered at least once per day or at least twice per day.

In certain embodiments, a compound of Formula (I) is present in a pharmaceutical composition in an amount of at least about 1% w/w. In other embodiments, the compound is present in a pharmaceutical composition in an amount of at least about 2.5% w/w, at least about 5% w/w, at least about 10% w/w, or at least about 15% w/w.

In yet other embodiments, a compound of Formula (I) is administered over a period of at least about one week. In certain embodiments, the compound is administered over a period of at least about four weeks.

These and other aspects of the present invention are explained with detail herein.

*p<0.05, ***P<0.001 vs. carrier by means of a single-factor analysis of variance (ANOVA) followed by a Student-Newman-Keuls post-analysis. Part B includes the contingency table obtained as a result of analyzing the possibilities of a tumor being present or absent at the end of an experiment according to receiving treatment with DHBS (100 mg/kg/day) or with DABS (100 mg/kg/day). The result of the analysis shows a $\chi^2$ value corresponding to p<0.05, which indicates that the probability of being tumor-free is significantly higher in the group treated with DABS.

Figure 6:
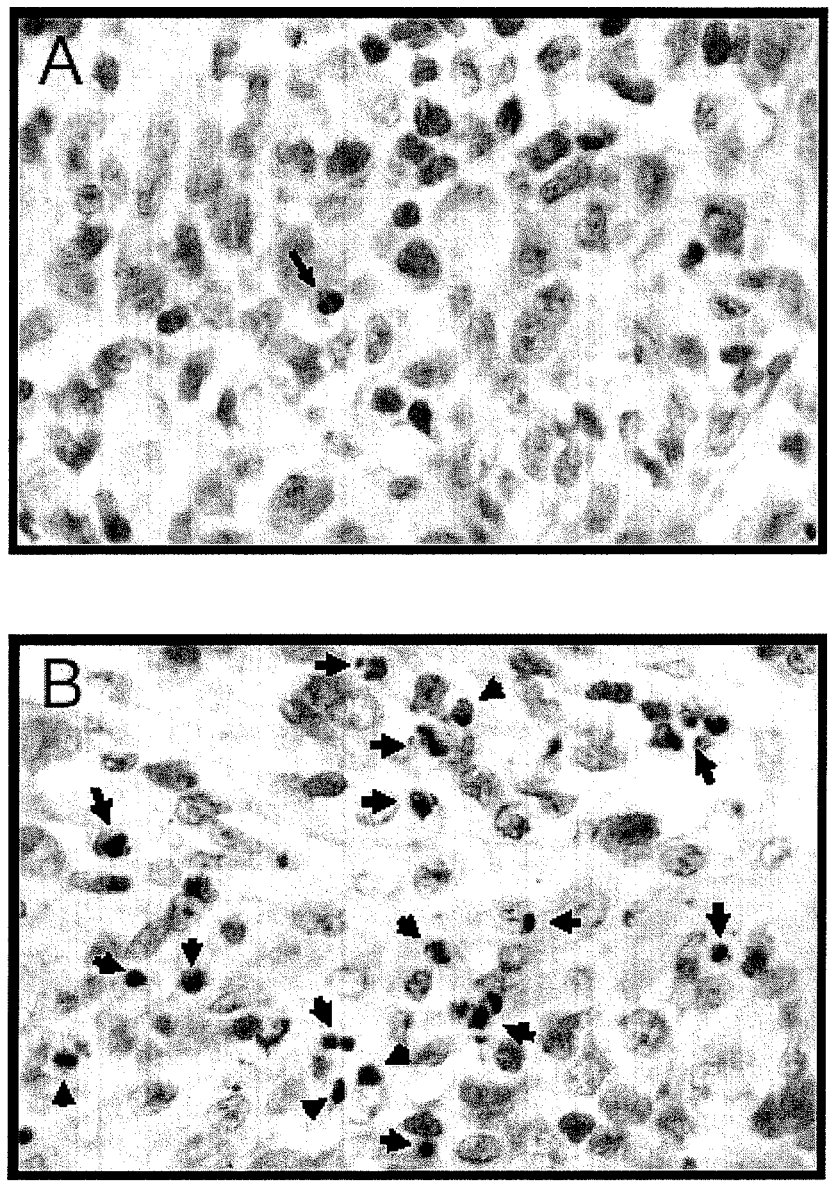

FIG. 6 shows the increase of apoptosis in the subcutaneous gliomas of rats treated with potassium 2,5-diacetoxybenzene sulfonate (DABS). The upper photograph shows a section of a tumor obtained from a rat treated with carrier (0.9% NaCl, i.p.) in which a low apoptosis index is observed (A). The lower photograph shows a section of a tumor obtained from a rat treated for days with DABS (100 mg/kg/day, i.p.) in which a large number of cells in an apoptosis process is observed (B). The sections are stained with hematoxylin and eosin and observed with a magnification of 313 times. The arrows indicate the cells in an apoptosis process.

Figure 7:
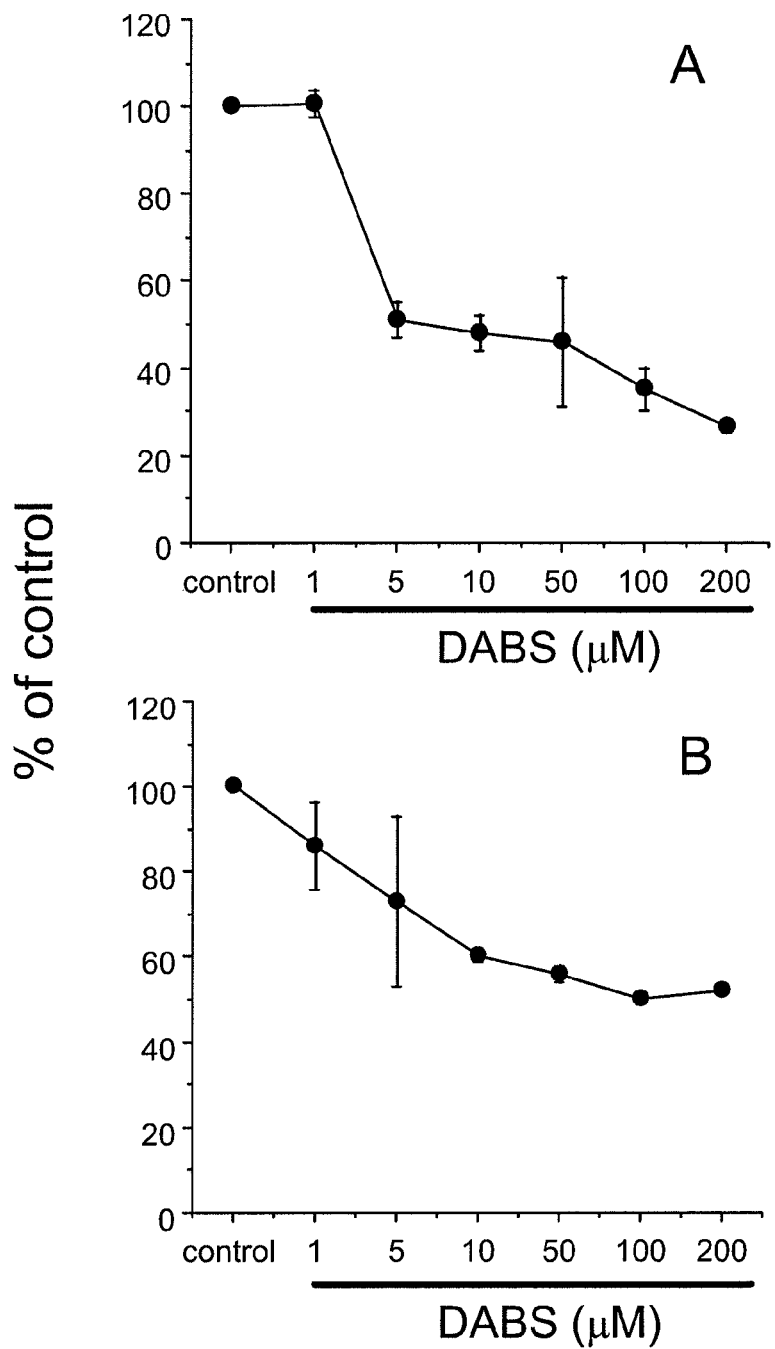

FIG. 7 shows the inhibition of human prostate cancer cell, PC-3 (A), and human lung cancer cell, A549 (B), proliferation by the treatment with potassium 2,5-diacetoxybenzene sulfonate (DABS; 1-200 µM). The number of viable cells was determined after 96 hours. The data were expressed as the mean±SEM of the percentage of the number of cells determined in the absence of DABS (control).

Figure 8:
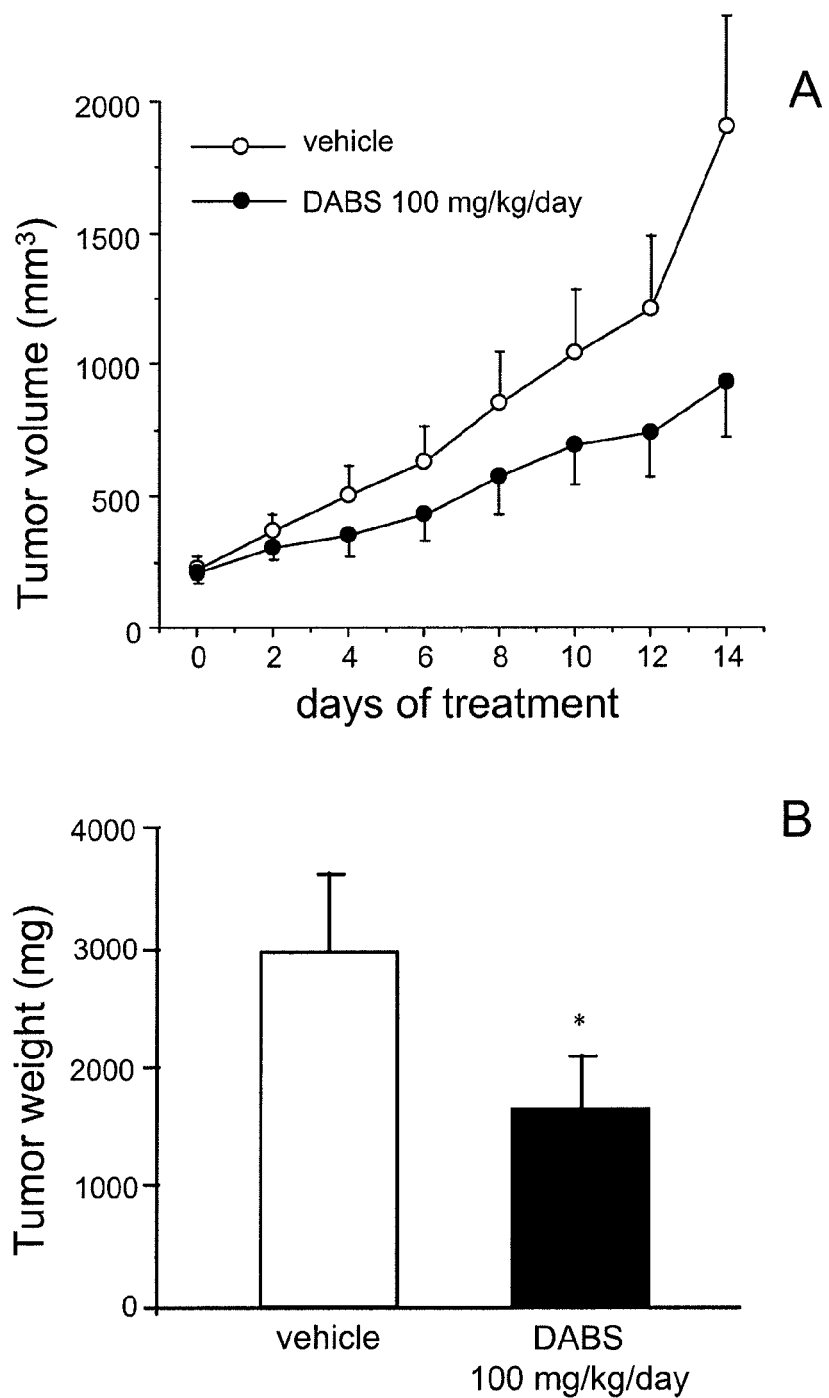

FIG. 8 shows the inhibition caused by potassium 2,5-diacetoxybenzene sulfonate (DABS; 100 mg/kg/day, i.p.) on the growth of subcutaneous human prostate cell tumors induced by the subcutaneous implantation of PC-3 cells in athymic mice. The implantation of tumor cells was carried out 10 days before starting the treatments. The carrier group received saline serum injections (0.9% NaCl, i.p.). The data correspond to 10 mice for each treatment. In panel A, the data are expressed as the mean±SEM of the tumor volume measured every 2 days through the skin with a Vernier caliper. The volume reduction caused by DABS reaches statistical significance. Panel B shows the effect of DABS on the weight of the tumor removed upon ending the assay. *p<0.05 by means of an unpaired Student's t test.

Figure 9:
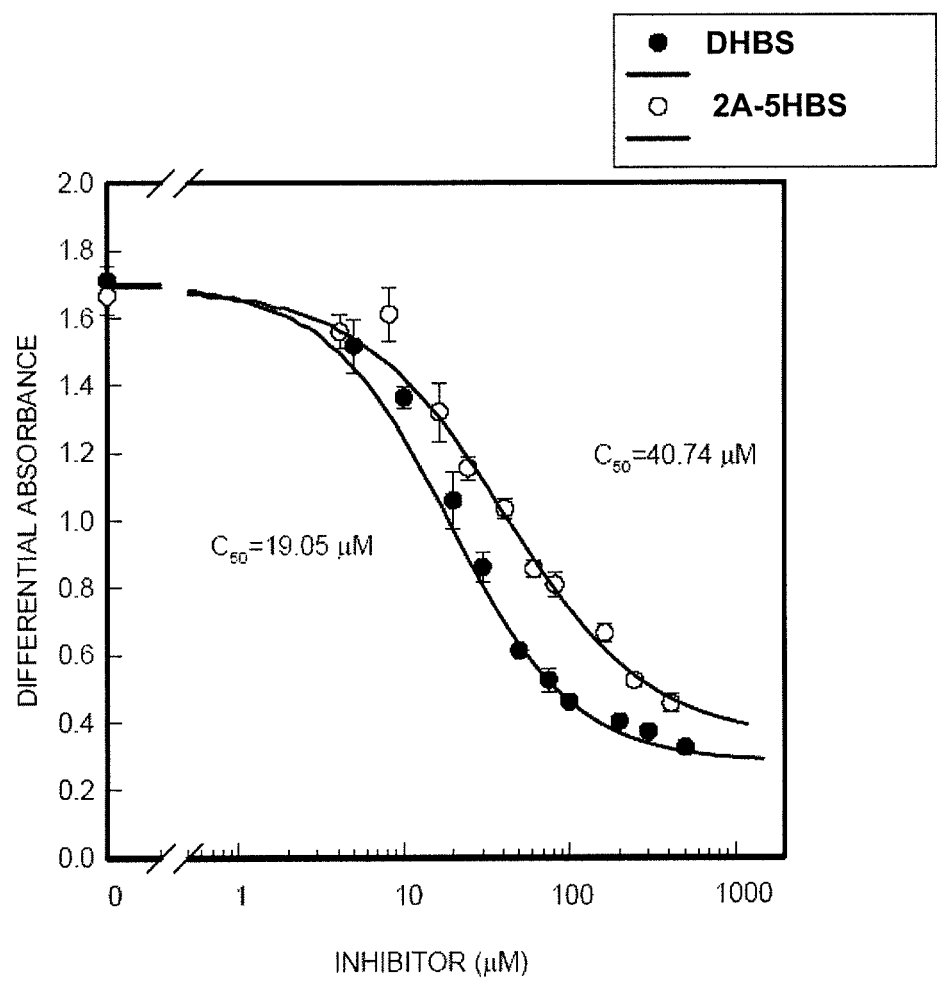

FIG. 9 shows the inhibition of the mitogenesis induced by fibroblast growth factor-1 in quiescent Balb/c 3T3 fibroblast cultures by calcium 2-acetoxy-5-hydroxybenzene sulfonate (2A5HBS) and potassium 2,5-dihydroxybenzene sulfonate (DHBS).

Figure 10:
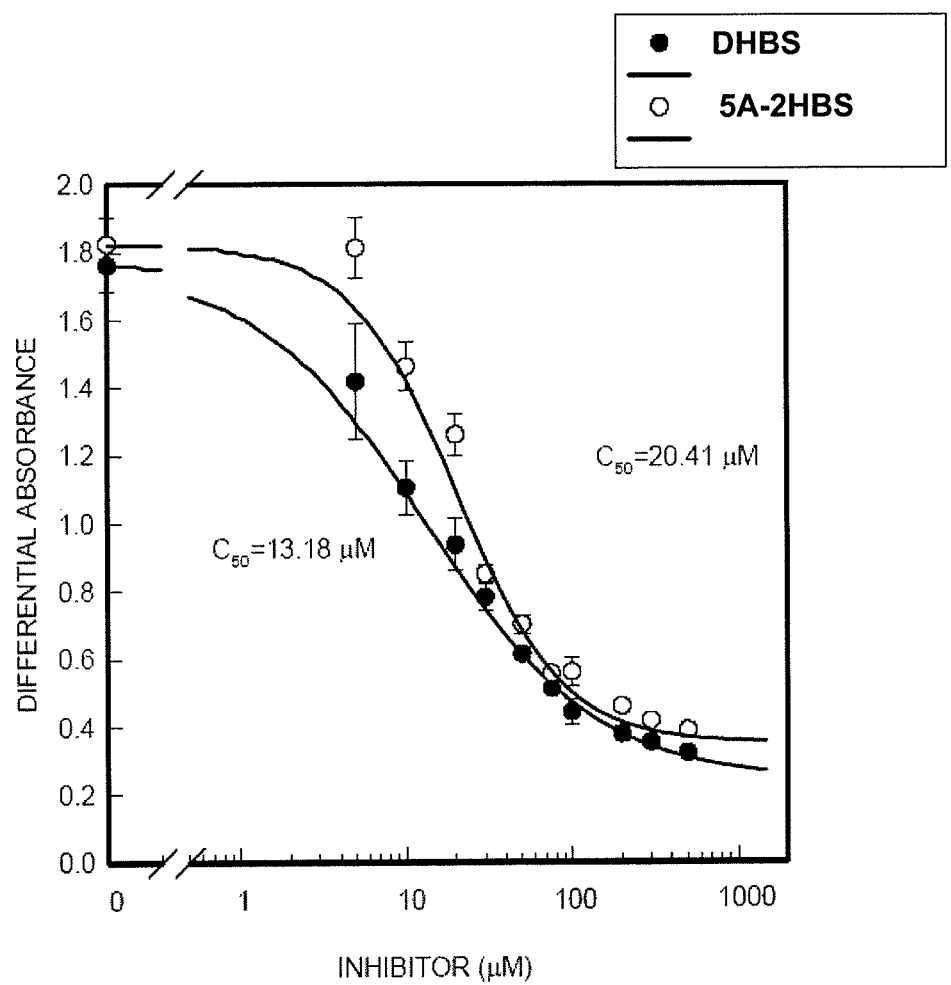

FIG. 10 shows the inhibition of the mitogenesis induced by fibroblast growth factor-1 in quiescent Balb/c 3T3 fibroblast cultures by potassium 5-acetoxy-2-hydroxybenzene sulfonate (5A-2HBS) and potassium 2,5-dihydroxybenzene sulfonate (DHBS).

Figure 11:
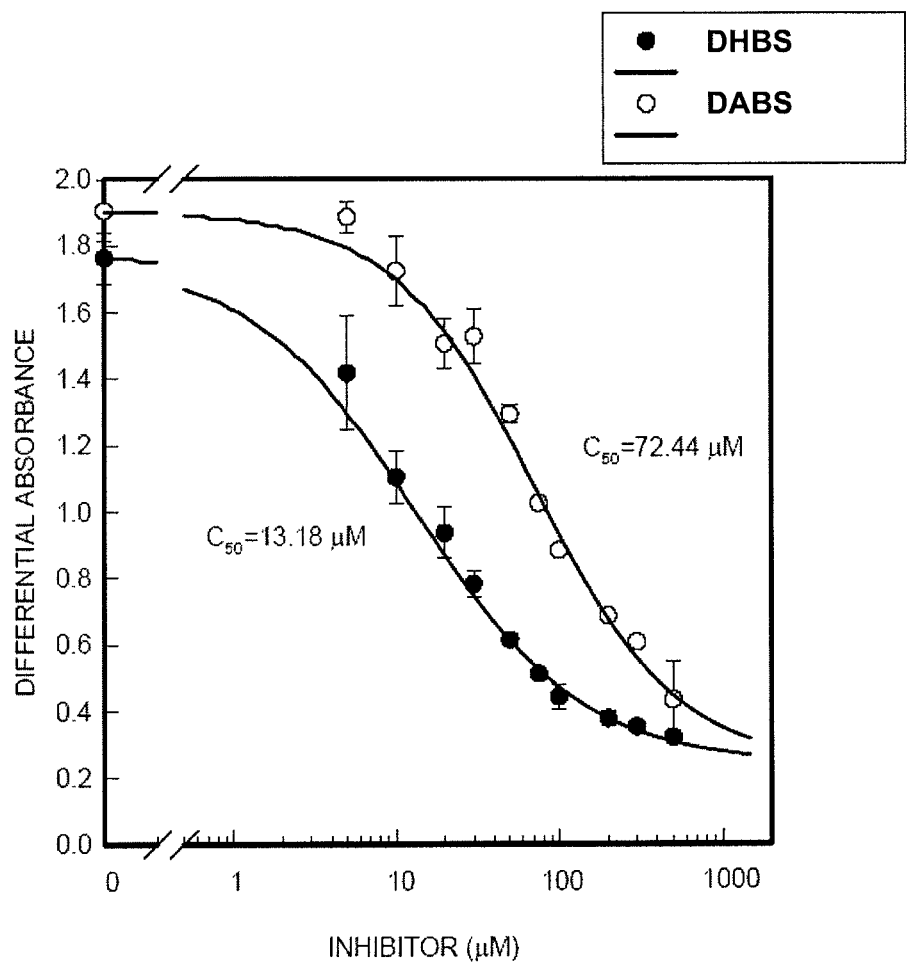

FIG. 11 shows the inhibition of the mitogenesis induced by fibroblast growth factor-1 III quiescent Balb/c 3T3 fibroblast cultures by potassium 2,5-diacetoxybenzene sulfonate (DABS) and potassium 2,5-dihydroxybenzene sulfonate (DHBS).

Figure 12:
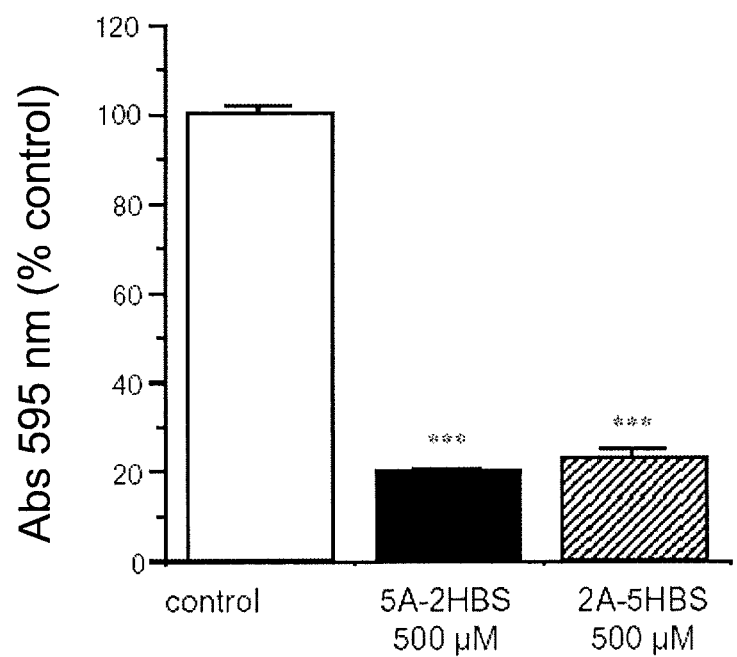

FIG. 12 shows the effect of the treatment with potassium 5-acetoxy-2-hydroxybenzene sulfonate (5-monoacetylated dobesilate; 5A-2HBS) and potassium 2-acetoxy-5-hydroxybencene sulfonate (2-monoacetylated dobesilate; 2A-5HBS) on the proliferation of rat glioma C6 cells. 5A-2HBS and 2A-5HBS were administered or not administered (control) after seeding the C6 cells in 24-well plates (104 per well) until they were fixed after 48 hours. The data are expressed as the mean±SEM of the percentage of the absorbance at 595 nm obtained in the control cultures, which is proportional to the number of cells stained with crystal violet. The data were obtained from 3 cultures for each treatment and 6 control cultures. The white bar represents the value of the control cells, whereas the black bar shows the value in the presence of 5A-2HBS (500 µM) and the striped bar shows the value in the presence of 2A-5HBS (500 µM). *** indicates p<0.001 with respect to the control by means of a single-factor analysis of variance (ANOVA) followed by a Student-Newman-Keuls post-analysis.

Figure 13:
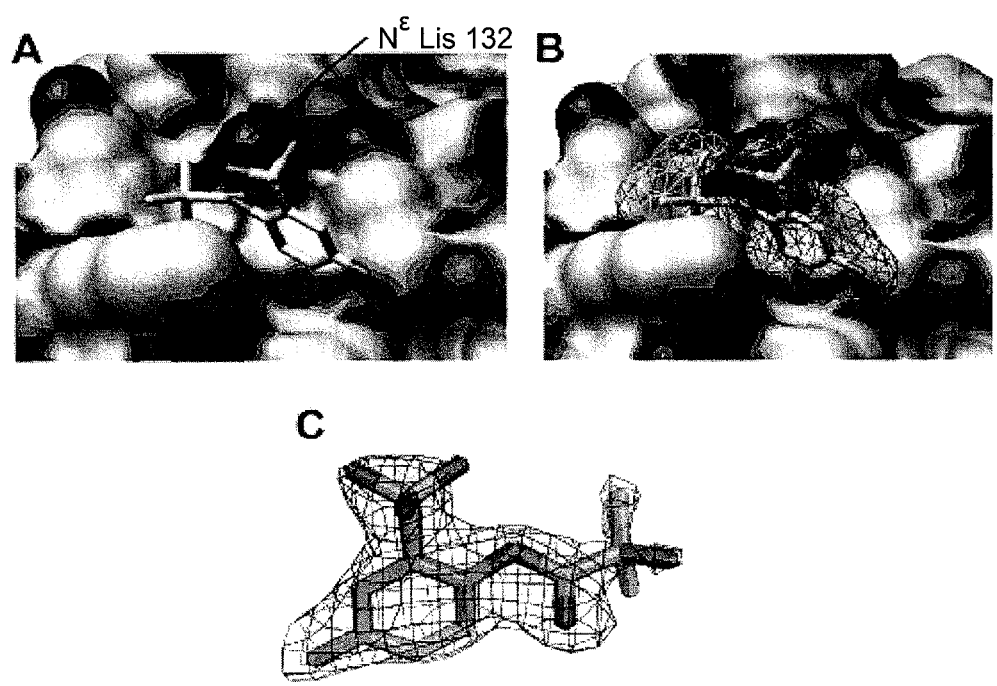

FIG. 13 shows 2-acetoxy-5-hydroxybenzenesulfonic acid co-crystallized with fibroblast growth factor-I. The electron density of the compound, contoured at 1cr (panel C), allows locating and determining the orientation of the compound with respect to the protein (panels A and B), as well as asserting that the compound conserves the acetoxyl group in position 2 when it binds to the protein. The compound occupies a place that is very close to that described occupied by 2,5-dihydroxybenzenesulfonic acid, the aromatic ring of which forms a cation-n bond with the $N^\epsilon$ group of lysine 132, which is marked in panel A as reference. Panel B shows, in the form of a mesh, the Van der Waals volume of 2-acetoxy-5-hydroxybenzenesulfonic acid, superimposed with its representation in the form of rods. In panels A and B, the protein surface is colored according to its electrostatic potential (light grey: negative charge; dark grey: positive charge; white: lack of charge).

Figure 14:
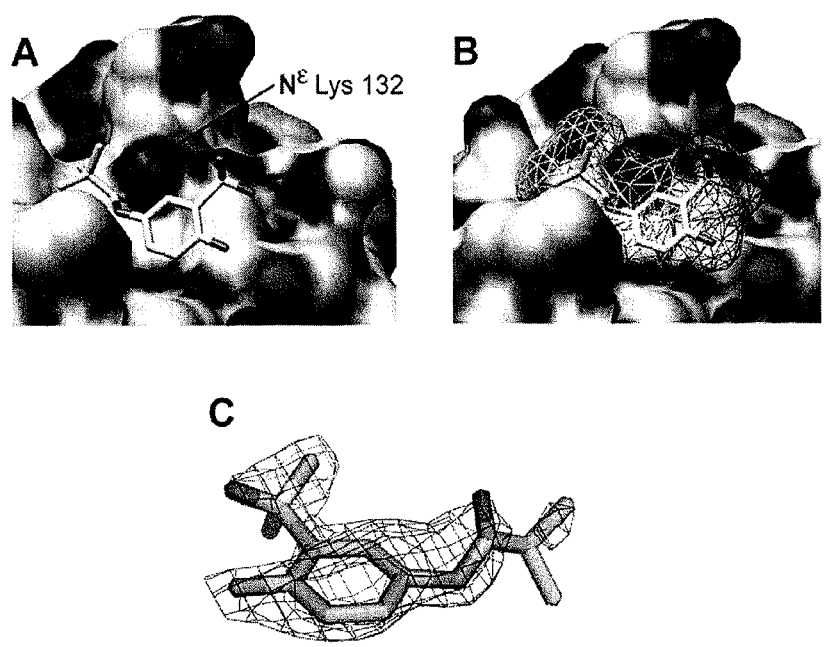

FIG. 14 shows 5-acetoxy-2-hydroxybenzenesulfonic acid co-crystallized with fibroblast growth factor-1. The electron density of the compound, contoured at 1 (J (panel C), allows locating and determining the orientation of the compound with respect to the protein (panels A and B), as well as asserting that the compound conserves the acetoxyl group in position 5 when it binds to the protein. The compound occupies a place that is very close to that described occupied by 2,5-dihydroxybenzenesulfonic acid, the aromatic ring of which forms a cation-n bond with the $N^\epsilon$ group of lysine 132, which is marked in panel A as reference. Panel B shows, in the form of a mesh, the Van der Waals volume of 2-acetoxy-5-hydroxybenzenesulfonic acid, superimposed with its representation in the form of rods. In panels A and B, the protein surface is colored according to its electrostatic potential (light grey: negative charge; dark grey: positive charge; white: lack of charge).

Figure 15:
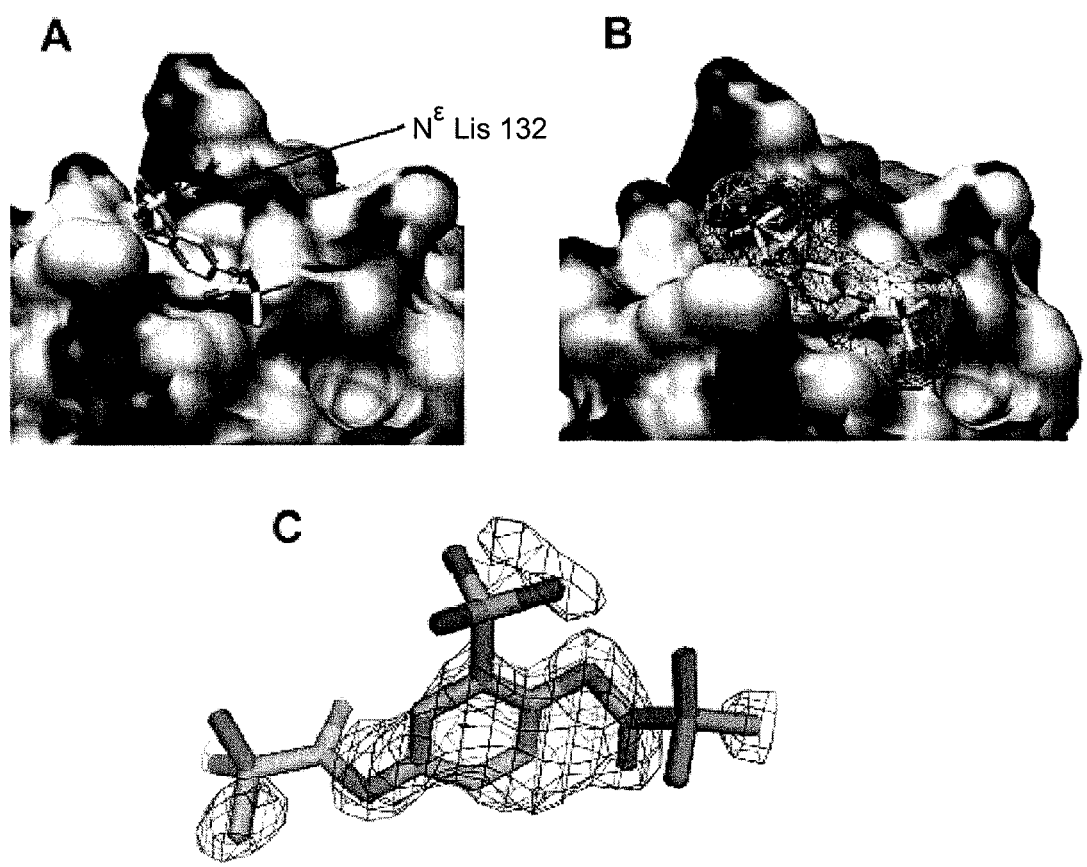

FIG. 15 shows 2,5-diacetoxybenzenesulfonic acid co-crystallized with fibroblast growth factor-1. The electron density of the compound, contoured at 1σ (panel C), allows locating and determining the orientation of the compound with respect to the protein (panels A and B), as well as asserting that the compound conserves the acetoxyl groups in positions 2 and 5 when it binds to the protein. The compound occupies a place that is very close to that described occupied by 2,5-dihydroxybenzenesulfonic acid, the aromatic ring of which forms a cation-n bond with the $N^\epsilon$ group of lysine 132, which is marked in panel A as reference. Panel B shows, in the form of a mesh, the Van der Waals volume of 2,5-diacetoxybenzenesulfonic acid, superimposed with its representation in the form of rods. In panels A and B, the protein surface is colored according to its electrostatic potential (light grey: negative charge; dark grey: positive charge; white: lack of charge).

DETAILED DESCRIPTION

As used throughout this description, it must be understood that the following terms have the following meanings unless otherwise indicated.

The term "patient" relates to animals, preferably mammals, more preferably human beings, and includes men and women, and children and adults.

The expression "effective amount" relates to the amount of the compound and/or composition which is effective for achieving its desired purpose.

The terms "treat" or "treatment" relate to the use of the compounds or compositions of the present invention in a prophylactic manner to prevent the symptoms of the disease or disorder, or in a therapeutic manner to improve an existing condition.

The term "cancer" relates to a disease or disorder characterized by uncontrolled cell division and the ability of these cells to invade other tissues by the direct growth in adjacent tissue through invasion or by the implantation in distant sites through metastasis.

The term "skin cancer" relates to and includes lentigo maligna, melanoma, keratoacanthoma, basal cell carcinoma (BCC), squamous cell carcinoma (SCC), Merkel cell carcinoma (MCC), sarcoma, angiosarcoma, cutaneous lymphoma, sweat gland carcinoma and sebaceous gland carcinoma.

The term "Merkel cell carcinoma (MCC)" refers to a neuroendocrine cancer that typically presents as a fast growing unspecific nodule on sun-exposed skin in people older than 65 years.

The term "sarcomas" refers to tumors of mesodermal origin affecting connective tissue of the skin, subcutaneous tissues or fascial sheaths. The more representative sarcomas affecting the skin are epithelioid cell sarcoma and angiosarcoma.

The term "cutaneous lymphoma" refers to tumors essentially consisting of dilated lymph channels of various sizes lined by normal lymph endothelium that may be present only in the skin, but frequently extend into subcutaneous fat and even muscle. The more frequent cutaneous lymphomas are cutaneous T-cell lymphomas and lymphangiomas.

The term "cancer of an organ" relates to and includes breast cancer, bladder cancer, colon cancer, rectal cancer, endometrial cancer, kidney cancer, lung cancer, cervical cancer, pancreatic cancer, prostate cancer, brain cancer, including ependymoma, glioma, glioblastoma, medulloblastoma, craneopharyngioma, pinealoma, acustic neuroma, retinoblastoma and meningioma; testicular cancer, thyroid cancer, ovarian cancer, Wilms' tumor, sarcoma and their metastasis.

The term "hematological dyscrasias" relates to and includes blood cancers, such as for example leukemia which includes acute lymphocytic leukemia, acute myelocytic leukemia, such as myeloblastic, promyeloblastic, myelomonocytic, erythrocytic leukemia and the like; chronic leukemia, such as chronic myelocytic (granulocytic) leukemia, chronic lymphocytic leukemia and the like; polycythemia vera, lymphoma (Hodgkin's disease and Non-Hodgkin's disease), multiple myeloma, Waldenstrom's macroglobulinemia, heavy chain disease and the like.

The term "myelodysplastic syndromes (MDSs)" refers to a hetegeroneous group of hematopoietic malignancies characterized by blood cytopenias, ineffective hematopoiesis and a hypercellular bone marrow. The MDSs are preleukemic conditions in which transformation into acute myeloid leukaemia (AML) occurs in approximately 30-40% of cases (Heaney M L, Godde D W. N *Engl. J. Med.* 1999). Unless an allogenic stem cell transplantation can be offered, MDS is generally considered to be an uncurable condition, and responses to chemotherapy and infrequent and short-lasting.

The term "chemotherapy" relates to the use of a chemotherapeutic agent for treating a cancer.

The term "radiation therapy" or "radiotherapy" relates to the medical use of ionization radiation as part of the cancer treatment to control cancer cells.

The expression "cancer immunotherapy" relates to the stimulation of the immune system to reject or destroy tumors, and includes but is not limited to immunotherapy with bacillus Calmette-Guerin (BCG), topical immunotherapy, immunotherapy by injection and the like.

The term "fibrosis" relates to and includes the excessive formation or development of fibrous connective tissue in an organ or tissue as a reactive or repairing process, in opposition to the formation of fibrous tissue as a normal constituent of an organ or tissue. Fibrosis includes but is not limited to endomyocardial fibrosis, idiopathic pulmonary fibrosis, emphysema, pulmonary fibrosis (leading to chronic obstructive pulmonary disease), Peyronie's disease, scleroderma, diffuse parenchymal lung disease, cheloids, mediastinal fibrosis, progressive massive fibrosis, proliferative fibrosis, neoplastic fibrosis, renal interstitial fibrosis, hepatic fibrosis, organ fibrosis, surgical scars or burns.

The term "therapeutic agent" includes any therapeutic agent that can be used to treat or prevent the diseases described herein. "Therapeutic agents" include but are not limited to chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FGF, VEGF, EGF or their respective receptors, a tyrosine kinase inhibitor, a protein kinase C inhibitor and a combination of two or more of them. A therapeutic agent includes pharmaceutically acceptable salts thereof, prodrugs and pharmaceutical derivatives thereof.

The term "antimicrobial compound" relates to any compound altering the growth of bacteria, fungi or viruses whereby the growth is prevented, modified, reduced, stabilized, inhibited or stopped. Antimicrobial compounds can be microbicides or microbiostatic agents and include but are not limited to antibiotics, semi-synthetic antibiotics, synthetic antibiotics, antifungal compounds, antiviral compounds and the like.

The term "antifungal compound" relates to any compound altering the growth of fungi whereby the growth is prevented, modified, reduced, stabilized, inhibited or stopped.

The term "antiviral compound" relates to any compound altering the growth of viruses whereby the growth is prevented, modified, altered, stabilized, inhibited or stopped.

The term "antioxidant" relates to and includes any compound that can react and inactivate a free radical, including but not limited to free radical eliminators, iron chelating agents, small molecule antioxidants and antioxidant enzymes and the like.

The term "taxane" relates to any compound containing the central carbon frame represented by Formula A:

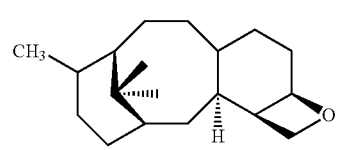

A

The term "NSAIDs" relates to a non-steroidal anti-inflammatory compound or to a nonsteroidal anti-inflammatory drug. NSAIDs inhibit cyclooxygenase, the enzyme responsible for the biosynthesis of prostaglandins and certain autacoid inhibitors, including inhibitors of several cyclooxygenase isozymes (including but not limited to cyclooxygenase 1 and 2), and inhibitors of both cyclooxygenase and lipoxygenase.

The term "organic cation" relates to a positively charged organic ion. Examples of organic cations include ammonium cations substituted with alkyl or unsubstituted ammonium cations, primary, secondary and tertiary amines, alkylamines, arylamines, cyclic amines, N,N'dibenzylethylenediamine and the like.

The term "inorganic cation" relates to a positively charged metal ion. Examples of inorganic cations include Group I metal cations such as, for example, sodium, potassium, magnesium, calcium and the like.

The expression "general charge" means the general or total charge of the compound.

The term "topical" relates to the administration of a compound by means of the application on the body surface and includes but is not limited to transdermal administration and administration through the mucous membrane.

The term "transdermal" relates to the administration of a compound passing through the skin into the blood stream.

The expression "through the mucous membrane" relates to the administration of a compound passing through the mucous tissue into the blood stream.

The term "parenteral" relates to the administration of a compound by subcutaneous, intravenous, intramuscular, intracardiac, intradermal, intraperitoneal, intrathecal or intracisternal injection, and also includes local and systemic infusion techniques.

The expression "penetration enhancement" or "permeation enhancement" relates to an increase in the permeability of the skin or mucous tissue for a pharmacologically active compound selected such that it increases the amount and/or the rate at which the compound penetrates the skin or mucous membranes or traverses the skin and mucous membranes.

"Excipients" or "carriers" relate to suitable carrier materials for the administration of a compound and include any of said materials known in the art such as for example, any liquid, gel, solvent, liquid diluent, solubilizer or the like, which is not toxic and does not interact with any component of the composition in a harmful manner.

The expression "sustained release" relates to the release of an active compound and/or composition such that the blood levels of the active compound are maintained in a desirable therapeutic interval for a time period. The sustained release formulation can be prepared using any conventional method known by persons skilled in the art to obtain the desired release characteristics.

The term "ester derivative of a compound of formula (I)" refers to the compound of formula (I) wherein at least one of Rg and Rg, is an ester group. For example, the ester derivative of 2,5-dihydroxybenzene sulfonic acid or dobesilate ester derivative refers to the compound, 5-dihydroxybenzene sulfonic acid (dobesilate) wherein at least one of the hydroxyl groups has been esterified.

The term "ester of a compound of formula (I)" refers to an ester of the sulfonic or carboxylic acid group at position 1. For example, the ester of 2,5-dihydroxybenzensulfonic acid or ester of dobesilate refers to an ester of the sulfonic acid group at position 1.

The following terms have the indicated meaning in the definitions of the compounds described herein:

"Alkyl" relates to a linear or branched chain hydrocarbon radical formed by hydrogen and carbon atoms, which does not contain unsaturations, with one to twelve, preferably one to eight, more preferably one to six carbon atoms and which is joined to the rest of the molecule by a single bond, for example, methyl, ethyl, n-propyl, i-propyl, n-butyl, t-butyl, n-pentyl, etc.

"Alkenyl" relates to a linear or branched chain hydrocarbon radical formed by hydrogen and carbon atoms, containing at least one unsaturation, with two to twelve, preferably two to eight, more preferably two to six carbon atoms and which is joined to the rest of the molecule by a single bond.

"Cycloalkyl" relates to a saturated carbocyclic ring having between three and eight, preferably three and six carbon atoms. It can have a bridged structure. Suitable cycloalkyl groups include but are not limited to cycloalkyl groups such as cyclopropyl, cyclobutyl, cyclopentyl or cyclohexyl.

"Aryl" relates to an aromatic hydrocarbon radical having from six to ten carbon atoms such as phenyl or naphthyl.

"Aralkyl" relates to an aryl group joined to the rest of the molecule by an alkyl group such as benzyl and phenethyl.

"Heterocycle" relates to a stable ring having 3 to 15 members consisting of carbon atoms and between one and five heteroatoms selected from the group consisting of nitrogen, oxygen and sulfur, preferably a ring having 4 to 8 members with one, two, three or four heteroatoms, more preferably a ring having 5 or 6 members with one, two or three heteroatoms. For the purposes of this invention, the heterocycle can be a monocyclic, bicyclic or tricyclic ring system, which can include fused ring systems; bridged structures; and the nitrogen, carbon or sulfur atoms in the heterocyclyl radical can optionally be oxidized; the nitrogen atom can optionally be quaternized; and the heterocyclyl radical can be partially or completely saturated or be aromatic. Examples of such heterocycles include but are not limited to azepines, benzimidazole, benzothiazole, furan, isothiazole, imidazole, indole, piperidine, piperazine, purine, quinoline, thiadiazole, tetrahydrofuran.

Unless otherwise indicated, the alkyl, cycloalkyl, alkenyl, alkynyl, aryl, aralkyl and heterocycle radicals can optionally be substituted with one, two or three substituents such as halo, alkyl, alkenyl, alkynyl, cycloalkyl, hydroxy, alkoxy, sulfoxy, O-benzyl, O-benzoyl, carboxy, alkylcarboxy, arylcarboxy, alkylcarbonyl, arylcarbonyl, cyano, carbonyl, acyl, alkoxycarbonyl, amino, alkylamino, dialkylamino, arylamino, diarylamino, alkylarylamino, imino, alkylsulfinyl, amidyl, carbamoyl, sulfonamido, nitro, nitrite, nitrate, thionitrate and carboxamido.

The term "alkoxycarbonyl" relates to compounds with the Formula —C(=O)O—, in which the C-end is joined to the molecule and the O-end is joined to a carbon atom to form an ester function. Said carbon atom can be part of an alkyl, alkenyl, cycloalkyl, alkynyl, aryl, aralkyl or heterocyclyl group.

The term "alkoxycarbonylalkyl" relates to compounds of Formula —C(=O)O— defined previously, in which the C-end is joined to the molecule through an alkyl group. The terms "aryloxy-arylalkoxy- or alkylarylalkoxy-carbonylalkyl" will be interpreted in a manner similar to the definition of "alkoxycarbonylalkyl".

The term "arylalkyl" relates to an aryl radical, as defined herein, joined to an alkyl radical, as defined herein. Examples of arylalkyl groups include benzyl, phenylethyl, 4-hydroxybenzyl, 3-fluorobenzyl, 2-fluorophenylethyl and the like.

The term "alkylaryl" relates to an alkyl group, as defined herein, to which an aryl group as defined herein is joined. Examples of alkylaryl groups include benzyl, phenylethyl, hydroxybenzyl, fluorobenzyl, fluorophenylethyl and the like.

The term "alkylsulfonyl" relates to $R_{50}—S(O)_2—$, where $R_{50}$ is a lower alkyl group as defined herein.

The term "arylsulfonyl" relates to $R_{55}$—$S(O)_2$—, where $R_{55}$ is an aryl group as defined herein.

The term "alkylsulfinyl" relates to $R_{55}$—$S(O)$—, where $R_{55}$ is an aryl group as defined herein.

The term "arylsulfinyl" relates to $R_{55}$—$S(O)$—, where $R_{55}$ is an aryl group as defined herein. The term "sulfonamide" relates to —$S(O)_2$—$N(R_{15})(R_{57})$, where $R_{51}$ and $R_{57}$ are each independently a hydrogen atom, an alkyl group, an aryl group, heterocyclic group, as defined herein, or $R_{51}$ and $R_{57}$ together form a heterocyclic ring, a cycloalkyl group, or a bridged cycloalkyl group, as defined herein.

The term "alkylsulfonamide" relates to a sulfonamido group as defined herein, bonded to an alkyl group as defined herein.

The term "arylsulfonamide" relates to a sulfonamido group as defined herein, bonded to an aryl group as defined herein.

The term "alkylcarbonyl" relates to $R_{52}$—$C(O)_2$—, where $R_{52}$ is an alkyl group as defined herein.

The term "arylcarbonyl" relates to the $R_{55}$—$C(O)$— radical, where $R_{55}$ is an aryl group as defined herein.

The term "carboxamide" relates to the —$C(O)N(R_{52})(R_{58})$ radical, where $R_{52}$ and $R_{58}$ are each independently a hydrogen atom, an alkyl group, an aryl group, or a heterocyclic group, as defined herein, or $R_{51}$ and $R_{57}$ together from a heterocyclic ring, a cycloalkyl group, or a bridged cycloalkyl group, as defined herein.

The term "carboxylic ester" relates to —$C(O)OR_{59}$, where $R_{59}$ is an alkyl group, an aryl group or a heterocyclic group, as defined herein.

The term "alkoxyalkyl" relates to an alkoxy group as defined herein, bonded to an alkyl group as defined herein. Examples of alkoxyalkyl groups are methoxymethyl, methoxyethyl, isopropoxymethyl and the like.

The term "amine" relates to any organic compound containing at least one basic nitrogen atom.

The term "prodrug" relates to compounds which are quickly transformed in vivo into pharmacologically active compounds. The design of prodrugs is generally studied in Hardma et al. (Eds.), Goodman and Gilman's The Pharmacological Basis of Therapeutics, 9th ed., pages 11-16 (1996). An in-depth study is carried out in Higuchi et al., Prodrugs as Novel Delivery Systems, Vol. 14, ASCD Symposium Series, and in Roche (ed.), Bioreversible Carriers in Drug Design, American Pharmaceutical Association and Pergamon Press (1987).

The compounds of the invention having one or more asymmetric carbon atoms can exist as optically pure enantiomers, pure diastereoisomers, mixtures of enantiomers, mixtures of diastereoisomers, racemic mixtures of enantiomers, diastereoisomeric racemates or mixtures of diastereoisomeric racemates. It must be understood that the invention foresees and includes all these isomers and mixtures thereof.

In a first aspect, the present invention relates to the use of a 2,5-dihydroxybenzene derivative represented by Formula (I) or a pharmaceutically acceptable salt or solvate thereof, isomer or prodrug thereof to prepare a medicament for the therapeutic and/or prophylactic treatment of skin cancer, wherein the compound of Formula (1) is:

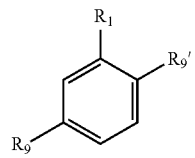

(I)

wherein:
$R_1$ is —$(CH_2)_aY$ or —$CH=CH$—$(CH_2)_pZ$;
Y is —$SO_3H$, —$SO_3^-.X^+$, —$SO_3R_3$, —$PO_3H$, —$PO_3^-.X^+$, —$PO_3R_3$;
Z is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;
$X^+$ is an organic cation or an inorganic cation, such that the general charge of the compound is neutral;
$R_9$ and $R_{9'}$ are independently selected from —OH and —$OR_2$, wherein when $R_9$ and $R_{9'}$ are both —$OR_2$, then said $R_9$ and $R_{9'}$, can be the same or different;
$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —$CH_2$—COOH, or a substituted or unsubstituted alkoxy-aryloxy-arylalkoxy- or alkylaryloxy-carbonylalkyl, in particular —$CH_2$—$COOR_3$;
$R_3$ is a substituted or unsubstituted alkyl group or a substituted or unsubstituted aryl group;
a is number selected from 0, 1, 2, 3, 4, 5 and 6;
P is an integer selected from 0, 1, 2, 3, 4, 5 and 6,
with the proviso that when Y is —$SO_3H$, —$SO_3^-.X^+$ or —$SO_3R_3$, then $R_9$ and $R_{9'}$ are independently selected from —OH and —$OR_2$, wherein at least one of R9 and R9' is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, the skin cancer is selected from the group consisting of lentigo maligna, melanoma, keratoacanthoma, basal cell carcinoma (BCC), squamous cell carcinoma (SCC), Merkel cell carcinoma (MCC), sarcoma, angiosarcoma, cutaneous lymphoma, sweat gland carcinoma and sebaceous gland carcinoma.

In another particular embodiment, 2,5-dihydroxybenzene derivatives of the invention or any of the pharmaceutically acceptable salts thereof are those that are represented by Formula (I) comprising dobesilate esters derivatives or pharmaceutically acceptable salts or esters thereof for the treatment of skin cancer or fibrosis.

The cation $X^+$ in the compounds of Formula (I) can be any physiologically acceptable cation known by a person skilled in the art, and includes but is not limited to those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the entire descriptions of which are incorporated as a reference herein. Cation X is selected such that the total charge of the compounds of Formula (I) is neutral.

In a particular embodiment of the invention $R_1$ is —$(CH_2)_a$Y or —CH=CH—$(CH_2)_p$Y. More particularly, Y in the compound of formula (I) is selected from —$SO_3H$, —$SO_3^-.X^+$ and —$SO_3R_3$.

In another embodiment, at least one of $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4methylphenylsulfonyl, benzylsulfonyl, benzyl and phenyl.

In another particular embodiment of the invention, $R_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C$_6$H$_4$Cl).

In another particular embodiment of the invention, $R_3$ is selected from methyl, ethyl, isopropyl and C6HS—, more particularly methyl and ethyl.

In an embodiment of the invention, the inorganic cation is sodium, potassium, lithium, calcium or magnesium.

In another embodiment of the invention, the organic cation is $[NH_{4-p}R_p]^+$, where p in each case is independently selected from an integer from 0 to 4; and R is an alkyl group of one to six carbon atoms such as, for example, methyl, ethyl, n-propyl, i-propyl, n-butyl, t-butyl or n-pentyl.

In another embodiment of the invention, the organic cations are a diethylamino group [H$_2$N$^+$(C$_2$H$_5$)$_2$], piperazine or pyridine.

In other embodiments of the invention, the compounds of Formula (I) and pharmaceutically acceptable salts thereof are:

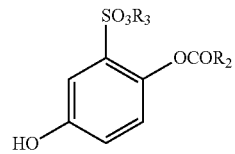
(1)

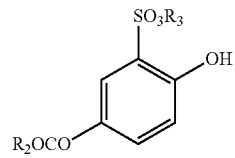
(2)

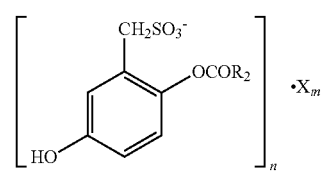
(3)

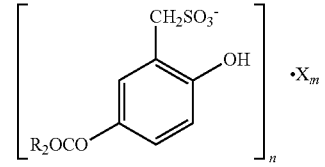
(4)

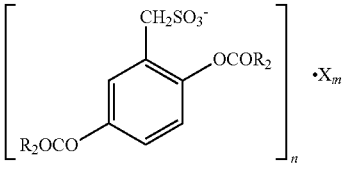
(5)

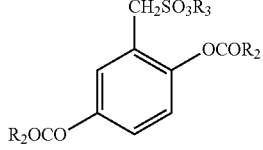
(6)

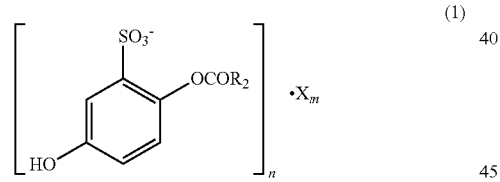
(7)

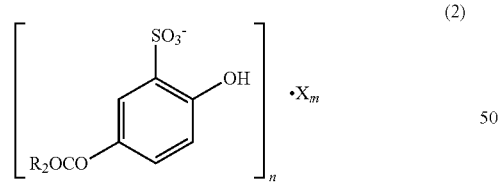
(8)

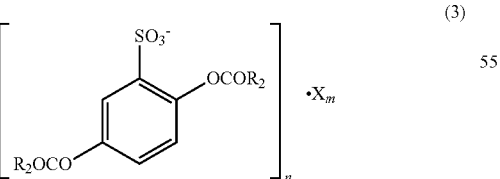
(9)

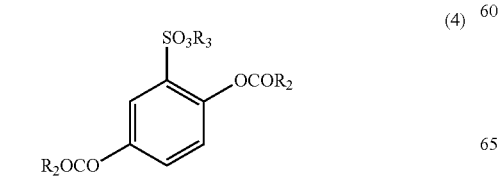
(10)

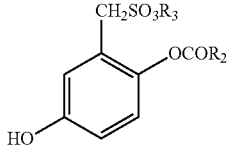
(11)

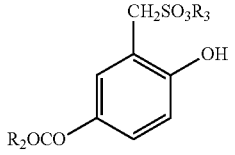
(12)

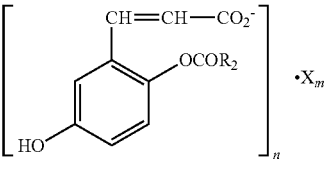
(13)

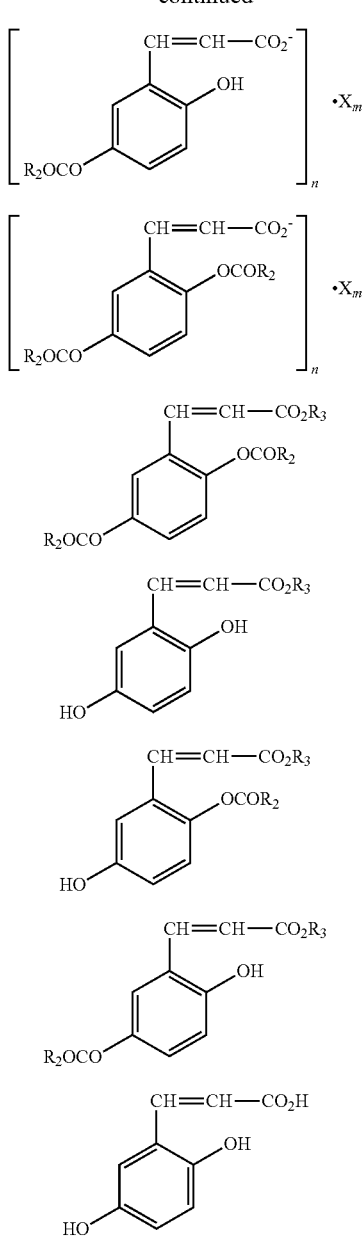

where:
n is an integer from 1 to 2;
m is an integer from 1 to 2; and
X, $R_2$ and $R_3$ are as defined herein.

In a preferred embodiment, the compound of Formula (I) is selected from the group consisting of:
5-hydroxy-2-{[(4-methylphenyl)sulfonyl]oxy}benzenesulfonic acid;
2-hydroxy-5-({[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

Particularly preferred are the compounds 2-(acetyloxy)-5-hydroxybenzenesulfonic acid; 5-(acetyloxy)-2-hydroxybenzenesulfonic acid and 2,5-bis(acetyloxy)benzenesulfonic acid.

The invention provides compositions comprising at least one compound of Formula (I) and at least one additional therapeutic agent, including but not limited to imiquimod, diclofenac, glycidic acid, trichloroacetic acid, colchicine, T4 endonuclease, 5-fluorouracil, isotretinoin, acitretin, cidofoir, 5-aminolevulinic acid, methyl aminolevulinate, hypericin, a chemotherapeutic agent, a corticosteroid, an antibiotic, an analgesic, an immunomodulator, an anti-angiogenic, including anti-VEGF, anti-FGF, anti-EGF and anti-HGF and their receptors; a leukotriene modifier, an aminosalicylate, an anesthetic, a non-steroidal anti-inflammatory, a therapy of the solubilized interleukin receptor, a cytotoxic, inhibitors of tyrosin-kinase receptors, protein kinase C inhibitors, and combinations of two or more thereof.

In an embodiment of the invention, the therapeutic agent includes anti-inflammatory compounds. The invention also provides said compositions in a pharmaceutically acceptable carrier.

In a particular embodiment, the therapeutic and/or prophylactic treatment of skin cancer is associated to photodynamic therapy, cryotherapy, curettage and surgery as a coadjuvant therapy.

The compounds of Formula (1) can optionally be used together with one or more additional therapeutic agents, such as a imiquimod, diclofenac, glycidic acid, trichloroacetic acid, colchicine, T4 endonuclease, 5-fluorouracil, isotretinoin, acitretin, cidofoir, 5-aminolevulinic acid, methyl aminolevulinate, hypericin, a chemotherapeutic agent, a corticosteroid, an antibiotic, an analgesic, an immunomodulator, an anti-angiogenic, including anti-VEGF, antiFGF, anti-EGF and anti-HGF and their receptors; a leukotriene modifier, an aminosalicylate, an anesthetic, a non-steroidal anti-inflammatory, a therapy of the solubilized interleukin receptor, a cytotoxic, inhibitors of tyrosin-kinase receptors, protein kinase C inhibitors, and combinations of two or more thereof.

In a second aspect, the present invention relates to the use of a compound of/Formula (I') or pharmaceutically acceptable salt or solvate, isomer or prodrug thereof in preparing a medicament for the treatment and/or prophylaxis of hematological dyscrasias, including myelodysplastic syndromes (MDSs) and for improving the efficacy of chemotherapy, radiation therapy and/or cancer immunotherapy; wherein the compound of Formula (I'):

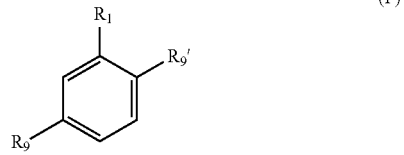

wherein:
$R_1$ is —$(CH_2)_a Y$ or —CH=CH—$(CH_2)_p Y$;
Y is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;
$X^+$ is an organic cation or an inorganic cation, such that the general charge of the compound is neutral;
$R_9$ and $R_{9'}$ are independently selected from —OH and —$OR_2$, wherein when $R_9$ and $R_{9'}$ are both —$OR_2$, then said $R_9$ and $R_{9'}$ can be the same or different;
$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group, a substituted or unsubstituted arylalkyl group, a substituted or unsubstituted alkylarylsulfonyl group, a substituted or unsubstituted arylalkylsulfonyl group, a substituted or unsubstituted aryloxyalkyl group, a carboxy group, a substituted or unsubstituted alkoxycarbonyl group, a substituted or unsubstituted carboxyalkyl group, particularly —$CH_2$—COOH, or a substituted or unsubstituted alkoxyaryloxy-arylalkoxy- or alkylaryloxy-carbonylalkyl group, particularly —$CH_2$—$COOR_3$,
$R_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6,
with the proviso that when Y is —$SO_3H$, —$SO_3^-.X^+$ or —$SO_3R_3$, then $R_9$ and $R_{9'}$ are independently selected from —OH and —$OR_2$, wherein at least one of $R_9$ and $R_{9'}$ is a Substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula (I') comprising dobesilate esters derivatives or pharmaceutically acceptable salts or esters thereof for the treatment of hematological dyscrasias, including myelodysplastic syndromes (MDSs) as well as for improving the efficacy of chemotherapy, radiation therapy and/or cancer immunotherapy.

The cation $X^+$ in the compounds of Formula (I') can be any physiologically acceptable cation known by a person skilled in the art, and includes but is not limited to those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the entire descriptions of which are incorporated as a reference herein. Cation X is selected such that the total charge of the compounds of Formula (I') is neutral.

In a particular embodiment of the invention Y in the compound of formula (I') is selected from —$SO_3H$, —$SO_3^-.X^+$, —$SO_3R_3$, —$CO_2H$, —$CO_2^-.X^+$ and —$CO_2R_3$.

In another particular embodiment, at least one of $R_9$ and $R_{9'}$ in the compound of formula (I') are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4methylphenylsulfonyl, benzylsulfonyl, benzyl and phenyl.

In another particular embodiment of the invention, $R_2$ is selected from acetyl (—$C(O)CH_3$), tosyl (—$SO_2$—$C_6H_4$—$CH_3$) and p-chlorophenoxyisobutyryl (—$C(O)$—$C(CH_3)_2$—O—$C_6H_4Cl$).

In another particular embodiment of the invention, $R_3$ is selected from methyl, ethyl, isopropyl and $C_6H_5$—, more particularly methyl and ethyl.

In an embodiment of the invention, the inorganic cation is sodium, potassium, lithium, calcium or magnesium.

In another embodiment of the invention, the organic cation is $[NH_{4-p}R_p]^+$, where p in each case is independently selected from an integer from 0 to 4; and R is an alkyl group of one to six carbon atoms such as, for example, methyl, ethyl, n-propyl, i-propyl, n-butyl, t-butyl or n-pentyl. In another embodiment of the invention, the organic cations are a diethylamino group $[H_2N^+(C_2H_5)_2]$, piperazine or pyridine.

In other embodiments of the invention, the compounds of Formula (I') and pharmaceutically acceptable salts thereof are:

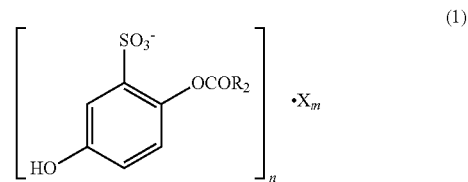

(1)

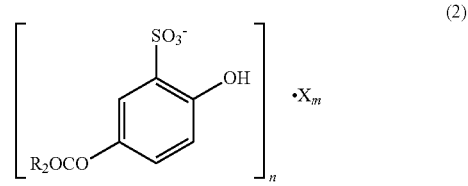

(2)

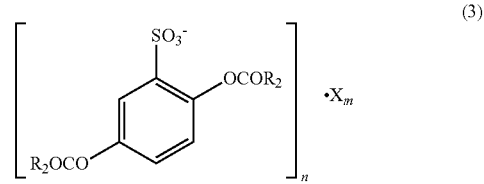

(3)

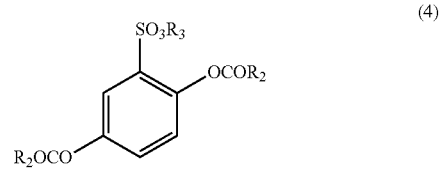

(4)

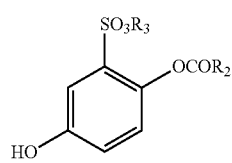 (5)
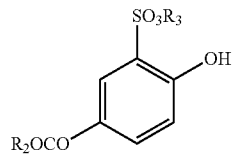 (6)
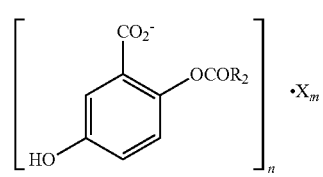 (7)
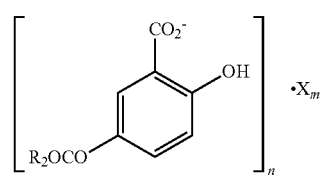 (8)
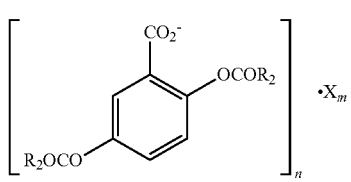 (9)
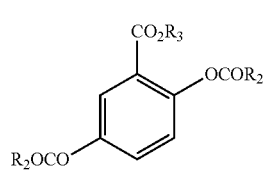 (10)
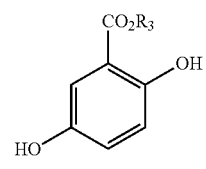 (11)
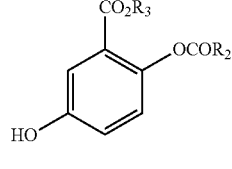 (12)
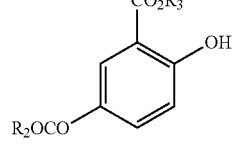 (13)
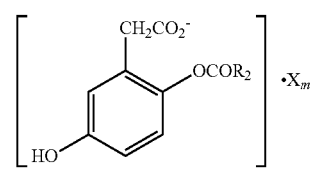 (14)
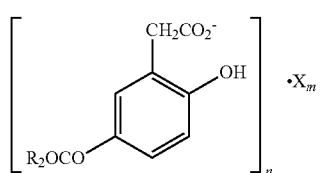 (15)
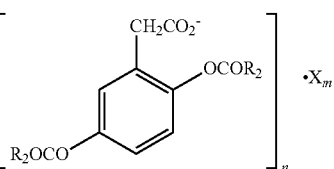 (16)
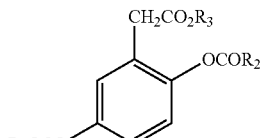 (19)
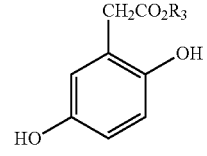 (20)
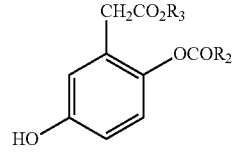 (21)
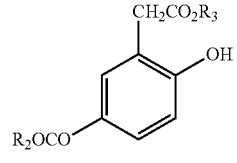 (22)
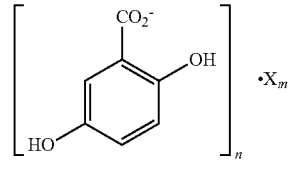 (23)
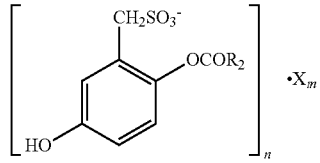 (24)

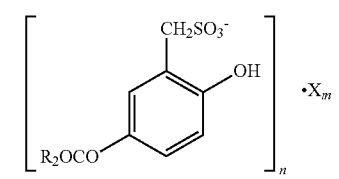 (25)

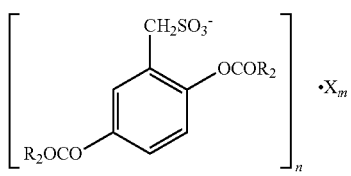 (26)

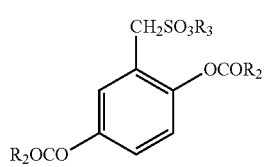 (27)

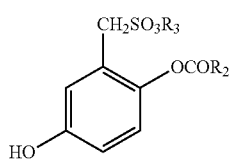 (28)

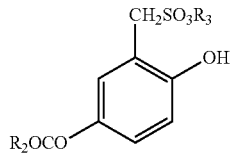 (29)

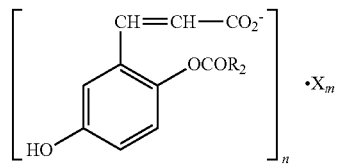 (30)

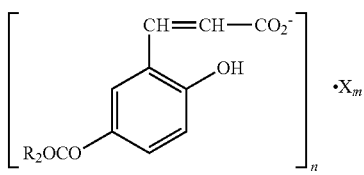 (31)

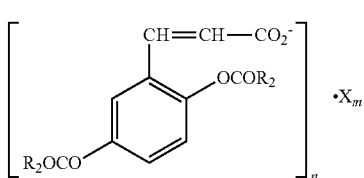 (32)

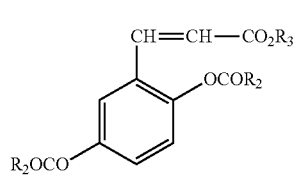 (33)

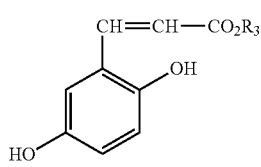 (34)

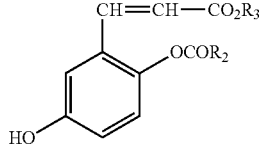 (35)

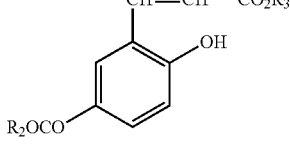 (36)

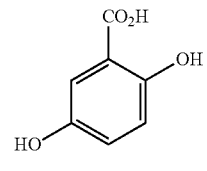 (37)

(38)

In a preferred embodiment, the compound of Formula (I') is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid.
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid.
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid), 5-hydroxy-2-{[(4-methylphenyl)sulfonyl]oxy}homobenzoic acid;

2-hydroxy-5-{[(4-methylphenyl)sulfonyl]oxy}homobenzoic acid;

2,5-bis{[(4-methylphenyl)sulfonyl]oxy}homobenzoic acid;

2-(acetyloxy)-5-hydroxyhomobenzoic acid;

5-(acetyloxy)-2-hydroxyhomobenzoic acid;

2,5-bis(acetyloxy)homobenzoic acid;

2-(benzyloxy)-5-hydroxyhomobenzoic acid;

5-(benzyloxy)-2-hydroxyhomobenzoic acid;

2,5-bis(benzyloxy)homobenzoic acid;

3-(2,5-dihydroxyphenyl)-2-propenoic acid (2,5-dihydroxycinnamic acid);

3-(5-hydroxy-2-{[(4-methylphenyl)sulfonyl]oxy}phenyl)-2-propenoic acid;

3-(2-hydroxy-5-{[(4-methylphenyl)sulfonyl]oxy}phenyl)-2-propenoic acid;

3-(2,5-bis{[(4-methylphenyl)sulfonyl]oxy}phenyl)-2-propenoic acid;

3-(2-(acetyloxy)-5-hydroxyphenyl)-2-propenoic acid;

3-(5-(acetyloxy)-2-hydroxyphenyl)-2-propenoic acid;

3-(2,5-bis(acetyloxy)phenyl)-2-propenoic acid;

3-(2-(benzyloxy)-5-hydroxyphenyl)-2-propenoic acid;

3-(5-(benzyloxy)-2-hydroxyphenyl)-2-propenoic acid;

3-(2,5-bis(benzyloxy)phenyl)-2-propenoic acid;

and pharmaceutically acceptable salts, solvates and prodrugs thereof.

Particularly preferred are the compounds 2-(acetyloxy)-5-hydroxybenzenesulfonic acid; 5(acetyloxy)-2-hydroxybenzenesulfonic acid and 2,5-bis(acetyloxy)benzenesulfonic acid.

The invention provides compositions comprising at least one compound of Formula (I') and at least one additional therapeutic agent, including but not limited to chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FOF, VEOF, EOF or their respective receptors, a tyrosine kinase inhibitor, a protein kinase C inhibitor and a combination of two or more of them.

The compounds of Formula (I') can optionally be used together with therapeutic agents, such as a chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FOF, VEOF, EOF or their respective receptors, a tyrosine kinase inhibitor, a protein kinase C inhibitor and a combination of two or more of them.

In a third aspect, the present invention refers to the use of a compound of Formula (I") or pharmaceutically acceptable salt or solvate, isomer or prodrug thereof in the manufacturing of a medicament for the treatment and/or prophylaxis of cancer of an organ, wherein the compound of Formula (I"):

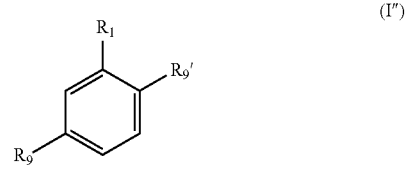

wherein:

$R_1$ is —$(CH_2)_a Y$ or —CH=CH—$(CH_2)_p Z$;

Y is —$SO_3H$, —$SO_3^-.X^+$, —$SO_3R_3$, —$PO_3H$, —$PO_3^-.X^+$, —$PO_3R_3$;

Z is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;

$X^+$ is an organic cation or an inorganic cation, such that the general charge of the compound is neutral;

$R_9$ and $R_{9'}$ are independently selected from —OH and —$OR_2$, wherein when $R_9$ and $R_{9'}$ are both —$OR_2$, then said $R_9$ and $R_{9'}$ can be the same or different;

$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group, a substituted or unsubstituted arylalkyl group, a substituted or unsubstituted alkylarylsulfonyl group, a substituted or unsubstituted arylalkylsulfonyl group, a substituted or unsubstituted aryloxyalkyl group, a carboxy group, a substituted or unsubstituted alkoxycarbonyl group, a substituted or unsubstituted carboxyalkyl group, particularly —$CH_2$—COOH, or a substituted or unsubstituted alkoxyaryloxy-arylalkoxy- or alkylaryloxy-carbonylalkyl group, particularly —$CH_2$—$COOR_3$, $R_3$ is a substituted or unsubstituted alkyl group or a substituted or unsubstituted aryl group;

a is number selected from 0, 1, 2, 3, 4, 5 and 6;

p is an integer selected from 0, 1, 2, 3, 4, 5 and 6.

with the proviso that when Y is —$SO_3H$, —$SO_3^-.X^+$ or —$SO_3R_3$, then $R_9$ and $R_{9'}$ are independently selected from —OH and —$OR_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula (I") comprising dobesilate esters derivatives or pharmaceutically acceptable salts or esters thereof for the treatment of cancer of an organ.

The cation $X^+$ in the compounds of Formula (I''') can be any physiologically acceptable cation known by a person skilled in the art, and includes but is not limited to those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the entire descriptions of which are incorporated as a reference herein. Cation X is selected such that the total charge of the compounds of Formula (I") is neutral.

In a particular embodiment of the invention Y in the compound of formula (I") is selected from —$SO_3H$, —$SO_3^-.X^+$ and —$SO_3R_3$.

In another particular embodiment, at least one of $R_9$ and $R_{9'}$ in the compound of formula ("I') are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4methylphenylsulfonyl, benzylsulfonyl, benzyl and phenyl.

In another particular embodiment of the invention, $R_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C$_6$H$_4$Cl).

In another particular embodiment of the invention, $R_3$ is selected from methyl, ethyl, isopropyl and C$_6$H$_5$—, more particularly methyl and ethyl.

In an embodiment of the invention, the inorganic cation is sodium, potassium, lithium, calcium or magnesium.

In another embodiment of the invention, the organic cation is [NH$_{4-p}$R$_p$]$^+$, where p in each case is independently selected from an integer from 0 to 4; and R is an alkyl group of one to six carbon atoms such as, for example, methyl, ethyl, n-propyl, i-propyl, n-butyl, t-butyl or n-pentyl.

In another embodiment of the invention, the organic cations are a diethylamino group [H$_2$N$^+$(C$_2$H$_5$)$_2$], piperazine or pyridine.

In other embodiments of the invention, the compounds of Formula (I") and pharmaceutically acceptable salts thereof are:

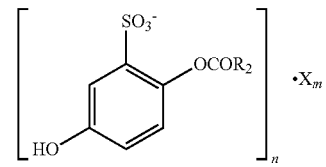

(1)

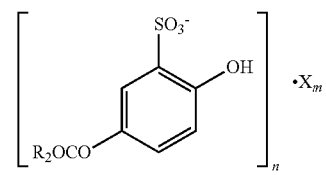

(2)

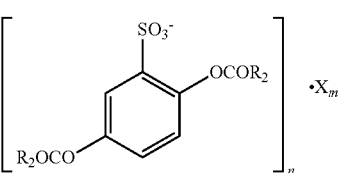

(3)

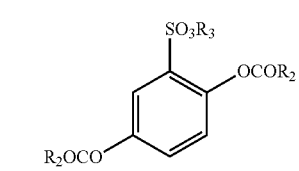

(4)

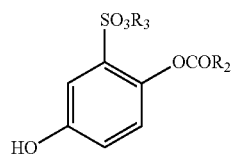

(5)

-continued

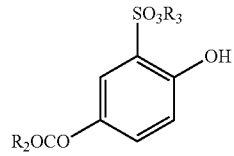

(6)

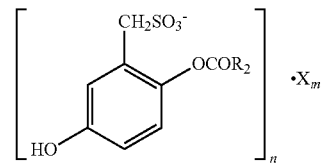

(7)

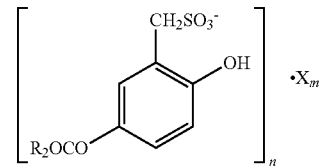

(8)

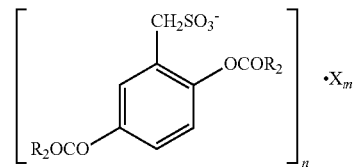

(9)

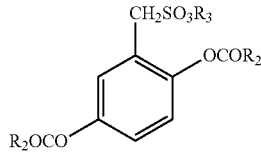

(10)

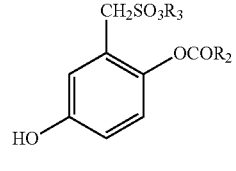

(11)

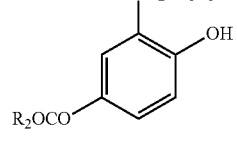

(12)

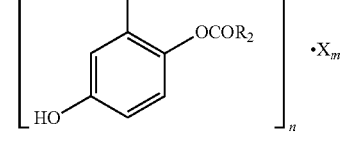

(13)

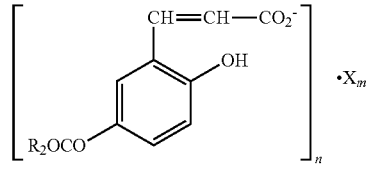

(14)

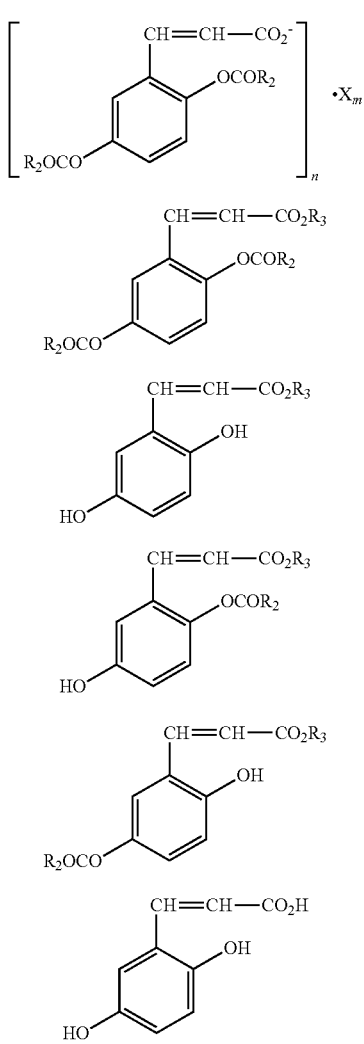

In a preferred embodiment, the compound of Formula (I″) is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid.
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid.
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

Particularly preferred are the compounds 2-(acetyloxy)-5-hydroxybenzenesulfonic acid; 5(acetyloxy)-2-hydroxybenzenesulfonic acid and 2,5-bis(acetyloxy)benzenesulfonic acid.

In another particularly embodiment, the cancer of an organ is selected form the group consisting of breast cancer, bladder cancer, colon cancer, rectal cancer, endometrial cancer, kidney cancer, lung cancer, cervical cancer, pancreatic cancer, prostate cancer, brain cancer, including ependymoma, glioma, glioblastoma, medulloblastoma, craneopharyngioma, pinealoma, acustic neuroma, retinoblastoma and meningioma; testicular cancer, thyroid cancer, ovarian cancer, Wilms' tumor, sarcoma and their metastasis.

The invention provides compositions comprising at least one compound of Formula (I″) and at least one additional therapeutic agent, including but not limited to chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FOF, VEOF, EOF or their respective receptors, a tyrosine kinase inhibitor, a protein kinase C inhibitor and a combination of two or more of them.

The compounds of Formula (I‴) can optionally be used together with one or more additional therapeutic agents, such as chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FGF, VEGF, EGF or their respective receptors, a tyrosine kinase inhibitor, a protein kinase C inhibitor and a combination of two or more of them.

In a fourth aspect, the present invention relates to the use of a 2,5-dihydroxybenzene derivative represented by Formula (I‴) or a pharmaceutically acceptable salt or solvate thereof, isomer or prodrug thereof to prepare a medicament for the therapeutic and/or prophylactic treatment of fibrosis, wherein the compound of Formula (I‴) is:

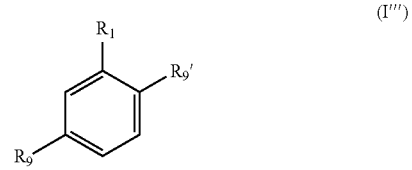

wherein:
$R_1$ is $-(CH_2)_aY$ or $-CH=CH-(CH_2)_pY$;
Y is $-SO_3H$, $-SO_3^-.X^+$, $-SO_3R_3$, $-PO_3H$, $-PO_3^-.X^+$, $-PO_3R_3$, $-CO_2H$, $-CO_2^-.X^+$ or $-CO_2R_3$;

$X^+$ is an organic cation or an inorganic cation, such that the general charge of the compound of Formula (I''') is neutral;

$R_9$ and $R_{9'}$ are independently selected from —OH and —OR$_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group;

and wherein when $R_9$ and $R_{9'}$ are both —OR$_2$, then said $R_9$ and $R_{9'}$ can be the same or different;

$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —CH$_2$—COOH, or a substituted or unsubstituted alkoxy-aryloxy-arylalkoxy- or alkylaryloxy-carbonylalkyl, in particular CH$_2$—COOR$_3$;

$R_3$ is a substituted or unsubstituted alkyl group or a substituted or unsubstituted aryl group;

a is number selected from 0, 1, 2, 3, 4, 5 and 6; and p is a number selected from 0, 1, 2, 3, 4, 5 and 6.

In a particular embodiment, 2,5-dihydroxybenzene derivatives of the invention or any of the pharmaceutically acceptable salts thereof are those that are represented by Formula (I''') comprising dobesilate esters derivatives or pharmaceutically acceptable salts or esters thereof for the treatment of fibrosis.

The cation $X^+$ in the compounds of Formula (I''') can be any physiologically acceptable cation known by a person skilled in the art, and includes but is not limited to those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the entire descriptions of which are incorporated as a reference herein. Cation X is selected such that the total charge of the compounds of Formula (I''') is neutral.

In a particular embodiment of the invention Y in the compound of formula (I''') is selected from —SO$_3$H, —SO$_3^-$.X$^+$ and —SO$_3$R$_3$, CO$_2$H, —CO$_2^-$.X$^+$ and —CO$_2$R$_3$. In another particular embodiment, $R_9$ and $R_{9'}$ in the compound of formula (I''') are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl.

In another particular embodiment of the invention, $R_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C$_6$H$_4$Cl).

In another particular embodiment of the invention, $R_3$ is selected from methyl, ethyl, isopropyl and C$_6$H$_5$—, more particularly methyl and ethyl.

In an embodiment of the invention, the inorganic cation is sodium, potassium, lithium, calcium or magnesium.

In another embodiment of the invention, the organic cation is [NH$_{4-p}$R$_p$]$^+$, where p in each case is independently selected from an integer from 0 to 4; and R is an alkyl group of one to six carbon atoms such as, for example, methyl, ethyl, n-propyl, i-propyl, n-butyl, t-butyl or n-pentyl.

In another embodiment of the invention, the organic cations are a diethylamino group [H$_2$N$^+$(C$_2$H$_5$)$_2$], piperazine or pyridine.

In other embodiments of the invention, the compounds of Formula (I''') and pharmaceutically acceptable salts thereof are:

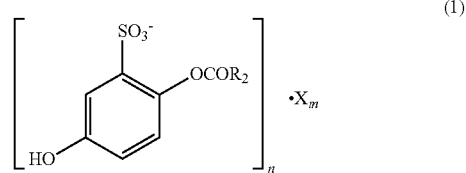

(1)

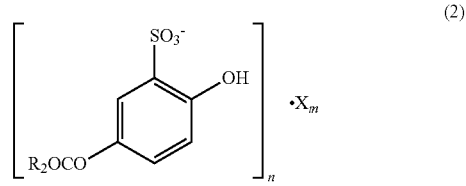

(2)

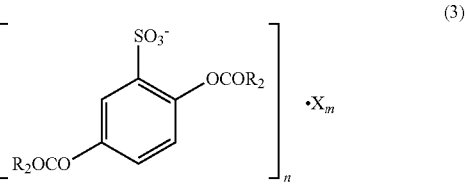

(3)

(4)

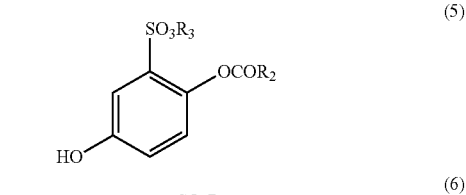

(5)

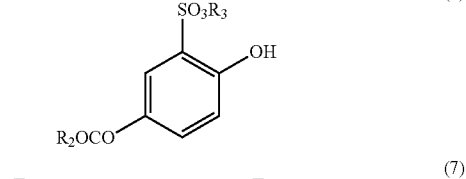

(6)

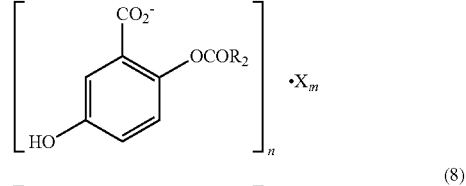

(7)

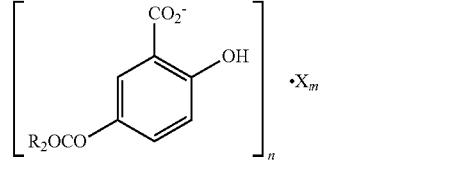

(8)

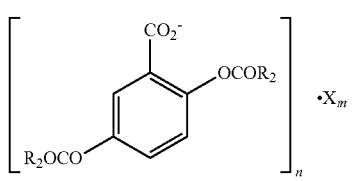 (9)
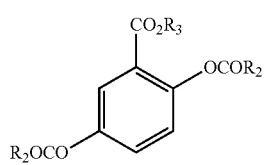 (10)
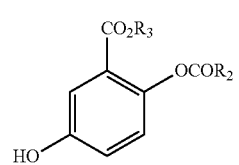 (11)
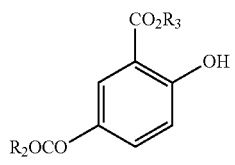 (12)
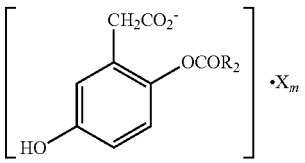 (13)
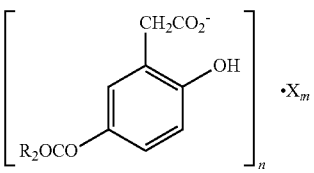 (14)
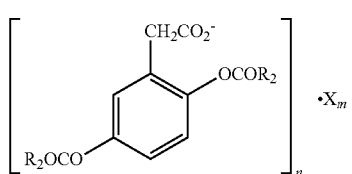 (15)
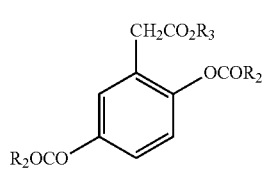 (16)
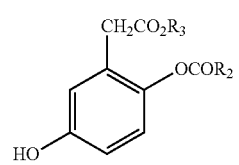 (17)
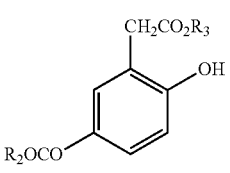 (18)
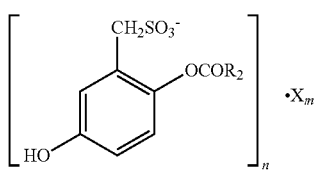 (19)
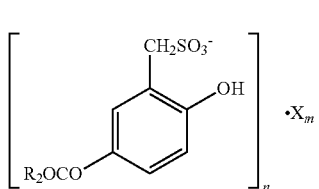 (20)
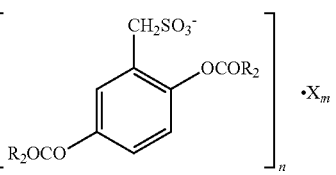 (21)
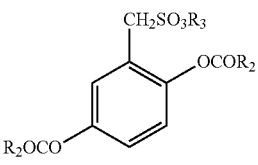 (22)
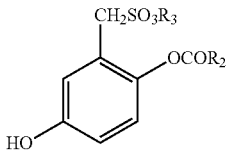 (23)
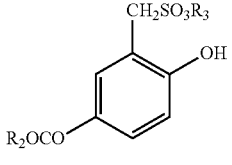 (24)
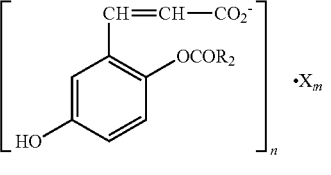 (25)
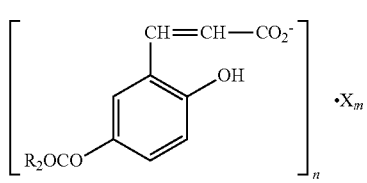 (26)

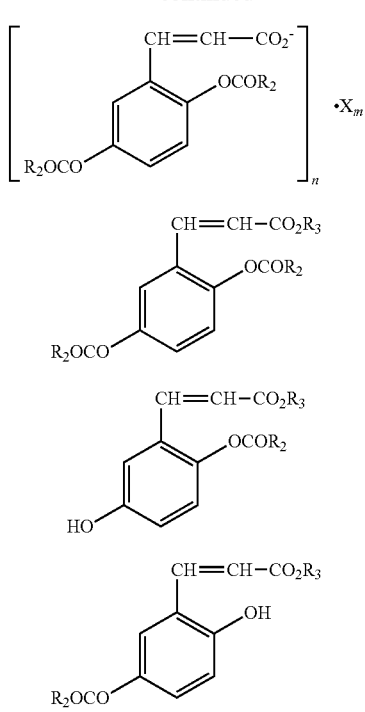

In a preferred embodiment, the compound of Formula (I''') is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
5-hydroxy-2-({[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
5-hydroxy-2-{[(4-methylphenyl)sulfonyl]oxy}homobenzoic acid;
2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy)homobenzoic acid;
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
and pharmaceutically acceptable salts, solvates and prodrugs thereof.

Particularly preferred are the compounds 2-(acetyloxy)-5-hydroxybenzenesulfonic acid; 5(acetyloxy)-2-hydroxybenzenesulfonic acid and 2,5-bis(acetyloxy)benzenesulfonic acid.

In another particular embodiment, the fibrosis includes endomyocardial fibrosis, idiopathic pulmonary fibrosis, emphysema, pulmonary fibrosis (leading to chronic obstructive pulmonary disease), Peyronie's disease, scleroderma, diffuse parenchymal lung disease, cheloids, mediastinal fibrosis, progressive massive fibrosis, proliferative fibrosis, neoplastic fibrosis, renal interstitial fibrosis, hepatic fibrosis, organ fibrosis, surgical scars or burns.

The invention provides compositions comprising at least one compound of Formula (I''') and at least one additional therapeutic agent, including but not limited to chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FGF, VEGF, EGF or their respective receptors, a tyrosine kinase inhibitor, a protein kinase C inhibitor and a combination of two or more of them.

The compounds of Formula (I''') can optionally be used together with one or more additional therapeutic agents, such as a chemotherapeutic agent, a steroid, a retinoid, an antimicrobial compound, an antioxidant, an anti-inflammatory compound, a vitamin D analog, salicylic acid, an NMDA receptor antagonist, an endothelin antagonist, an immunomodulating agent, an angiogenesis inhibiting/blocking agent, a compound inhibiting FGF, VEGF, EGF or their respective receptors, a tyrosine kinase inhibitor, a protein kinase C inhibitor and a combination of two or more of them.

The compounds of Formula (I), (I'), (I'') and (I''') can be synthesized by a person skilled in the art using conventional methods available on the market. The synthesis of the compounds of Formula (I), (I'), (I'') and (I''') is described, for example, in U.S. Pat. No. 5,082,941; and "The Merck Index" 13th edition, Merck & Co., R. Railway, N.J., USA, 2001; U.S. Pat. Nos. 5,082,841, 4,814,110, 4,613,332 and 4,115,648; the entire descriptions of which are incorporated as a reference herein.

The compounds of Formula (I), (I'), (I'') and (I''') can also be in the form of solvates, particularly in the form of hydrates. The compounds of Formula (I), (I'), (I'') and (I''') as well as their solvates can be prepared by a person skilled in the art using conventional methods and reagents available on the market.

Although it was previously indicated in one of the preferred embodiments with respect to the definition of cation X, the scope of this invention includes any salt thereof, particularly any pharmaceutically acceptable salt of the compound. The term "pharmaceutically acceptable salts" includes the metal salts or the addition salts which can be used in dosage forms. For example, the pharmaceutically acceptable salts of the compounds provided herein can be acid addition salts, base addition salts or metal salts, and can be synthesized from parent compounds containing a basic or acid residue by means of conventional chemical processes. Such salts are generally prepared, for example, by reacting the free acid or base forms of these compounds with a stoichiometric amount of the suitable base or acid in water or in an organic solvent or in a mixture of both. Non-aqueous media are generally preferred, such as ether, ethyl acetate, ethanol, isopropanol, or acetonitrile. Examples of acid addition salts include mineral acid additions salts such as, for example, hydrochloride, hydrobromide, hydroiodide, sulfate, nitrate, phosphate, organic acid addition salts such as, for example, acetate, maleate, fumarate, citrate, oxalate, succinate, tartrate, malate, mandelate, methanesulfonate and p-toluenesulfonate. Examples of alkali addition salts include inorganic salts such as, for example, ammonium salts and organic alkaline salts such as, for example, diethylamine, ethylenediamine, ethanolamine, N,Ndialkylenethanolamine, triethanolamine, glutamine and basic amino acid salts. Examples of metal salts include, for example, sodium, potassium, calcium, magnesium, aluminium and lithium salts.

The term "pharmaceutically acceptable" relates to molecular entities and compositions that are physiologically tolerable and do not normally cause an allergic reaction or a similar adverse reaction, such as gastric discomfort, dizziness and the like, when administered to humans. As used herein, the term "pharmaceutically acceptable" preferably means that it is approved by a regulatory agency of the federal or state government or listed in the US pharmacopoeia or another pharmacopoeia, generally recognized for its use in animals and more particularly in human beings.

It will be evident for persons skilled in the art that the scope of the present invention also comprises salts that are not pharmaceutically acceptable as possible means for obtaining pharmaceutically acceptable salts.

According to this invention, the term "solvate" must be understood to mean any form of the active compound according to the invention having another molecule (most likely a polar solvent) joined thereto by means of a non-covalent bond. Examples of solvates include hydrates and alcoholates, preferably C1-C6 alcoholates, methanolate for example.

The pharmaceutically acceptable salts of the compounds of Formula (I), (I'), (I") and (I''') can be obtained from organic or inorganic acids or bases by conventional methods by reacting the suitable acid or base with the compound.

In a particular embodiment of the invention, the 2,5-dihydroxybenzene derivatives of the invention can optionally be used combining them with one another. Said combinations can be in the same formulation or in formulations which would be sequentially used.

In certain embodiments, the invention provides a composition comprising an ester derivative of those comprised in Formula (I), (I'), (I") and (I'''), particularly a dobesilate ester derivative, such as 2-acetyloxy-5-hydroxybenzenesulfonic acid, 5-acetyloxy-2hydroxybenzenesulfonic acid, or 2,5-bis-acetyloxybenzene sulfonic acid. In some embodiments, it will be desirable to formulate a composition of the invention with an active ingredient which is a dobesilate ester derivative, for example, where the ester derivative shows greater therapeutic efficacy than the original compound in the treatment or prevention of a condition described herein. In other embodiments, the invention includes the use of a dobesilate ester derivative as a prodrug, for example, to treat a condition described herein, in which the ester is metabolized to the original compound in a patient for the purpose of reaching therapeutic efficacy in the patient.

Suitable chemotherapeutic agents include but are not limited to alkylating agents such as, for example, cyclophosphamide, carmustine, daunorubicin, mechlorethamine, chlorambucil, nimustine, melphalan and the like; anthracyclines, such as, for example, daunorubicin, doxorubicin, epirubicin, idarubicin, mitoxantrone, valrubicin and the like; taxane compounds, such as, for example, paclitaxel, docetaxel and the like; topoisomerase inhibitors such as, for example, etoposide, teniposide, tuliposide and the like; nucleotide analogs such as, for example, azacitidine, azathioprine, capecitabin, cytarabine, doxifluridine, fluorouracil, gemcitabine, mercaptopurine, methotrexate, thioguanine and the like; platinum-based agents such as, for example, carboplatin, cisplatin, oxaliplatin and the like; antineoplastic agents such as, for example, vincristine, leucovorin, lomustine, procarbazine and the like; hormone modulators such as, for example, tamoxifen, finasteride, 5-a-reductase inhibitors and the like; vinca alkaloids such as, for example, vinblastine, vincristine, vindesine, vinorelbine and the like. Suitable chemotherapeutic agents are described in more detail in the literature, such as in The Merck Index on CD-ROM, 13th Edition.

In some embodiments of the invention, the chemotherapeutic agents are 5-fluorouracil, tamoxifen, paclitaxel, cisplatin, carboplatin, carmustine, nimustine, leucovorin, gemcitabine, docetaxel, vincristine, vinblastine, vinorelbine, vindesine, irinotecan, vinca alkaloids or topoisomerase inhibitors.

Suitable steroids include but are not limited to budesonide, dexamethasone, corticosterone, prednisolone and the like. Suitable steroids are described in more detail in the literature, such as in The Merck Index on CD-ROM, 13th Edition. In a preferred embodiment of the invention, the steroids are dexamethasone, prednisolone and corticosteroids.

Suitable retinoids include but are not limited to natural and synthetic analogs of vitamin A (retinol), vitamin A aldehyde (retinal), vitamin A acid (retinoic acid (RA)), including all the trans-, 9-cis- and 13-cis-retinoic acids), tretinoin, isotretinoin, alitretinoin, etretinate, acitretin, tazarotene, bexarotene and the like. Suitable retinoids are also described in document EP 0379367 A2, U.S. Pat. Nos. 4,887,805; 4,888,342; 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130; 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753 and the like; the entire descriptions of which are incorporated herein as a reference. In some preferred embodiments of the invention, the retinoids are retinol, retinal, retinoic acid, tretinoin, isotretinoin or alitretinoin.

Suitable antimicrobial compounds include but are not limited to macrolides such as, for example, azithromycin, clarithromycin, dirithromycin, erythromycin, milbemycin, troleandomycin and the like; monobactams such as, for example, aztreonam and the like; tetracyclines such as, for example, demeclocycline, doxycycline, minocycline, oxytetracycline, tetracycline and the like; aminoglycosides such as, for example, amikacin, gentamicin, kanamycin, neomycin, netilmicin, paromomycin, streptomycin, tobramycin and the like; carbacephems such as, for example, loracarbef and the like; carbapenems such as, for example, ertapenem, imipenem, meropenem and the like; penicillins such as, for example, amoxicillin, ampicillin, azlocillin, carbenicillin, cloxacillin, dicloxacillin, flucloxacillin, mezlocillin, nafcillin, penicillin, piperacillin, ticarcillin and the like; polypeptides such as, for example, bacitracin, colistin, polymyxin B and the like; beta-lactamase inhibitors; cephalosporins such as, for example, cefaclor, cefamandole, cefoxitin, cefprozil, cefuroxime, cefixime, cefdinir, cefditoren, cefoperazone, cefotaxime, cefpodoxime, cefadroxil, ceftazidime, ceftibuten, ceftizoxime, ceftriaxone, cefazolin, cephalaxin, cefepime and the like; quinolones such as, for example, ciprofloxacin, enoxacin, gatifloxacin, levofloxacin, lomefloxacin, moxifloxacin, norfloxacin, ofloxacin, trovafloxacin and the like; streptogramins; sulfonamides such as, for example, mafenide, prontosil, sulfacetamide, sulfamethizole, sulfanilamide, sulfasalazine, sulfisoxazole, trimethoprim, trimethoprim-sulfamethoxazole and the like; and the combination drugs such as, for example, sulfamethoxazole and trimethoprim and the like. Suitable antimicrobial compounds of the invention are more fully described in the literature, such as in Goodman and Gilman, The Pharmacological Basis of Therapeutics (9th Edition), McGraw-Hill, (1996); Merck Index on CD-ROM, 13th Edition; STN Express, file phar and file registry, the entire descriptions of which are incorporated herein as a reference. In some preferred embodiments of the invention, the antimicrobial compounds are tetracycline, erythromycin or clindamycin.

Suitable antioxidants include but are not limited to free radical eliminators, iron chelating agents, small molecule antioxidants and antioxidant enzymes and the like. Suitable iron chelating agents include but are not limited to deferoxamine, deferiprone, dithiocarbamate, ethylenediaminetetraacetic acid and the like. Suitable small molecule antioxidants include but are not limited to compounds of hydralazine, glutathione, ascorbic acid (vitamin C), vitamin E, cysteine, N-acetyl-cysteine, ~-carotene, ubiquinone, ubiquinol-10, tocopherols, coenzyme Q, superoxide dismutase mimetics such as, for example, 2,2,6,6-tetramethyl-1-piperidinyloxy (TEMPO), DOXYL, PROXYL nitroxide compounds; 4-hydroxy-2,2,6,6-tetramethyl-piperidinyloxy (TEMPOL), M-40401, M-40403, M-40407, M-40419, M-40484, M-40587, M40588 and the like. Suitable antioxidant enzymes include but are not limited to superoxide dismutase, catalase, glutathione peroxidase, NADPH oxidase inhibitors such as, for example, apocynin, aminoguanidine, ONO 1714, SI7834 (a benzo(b)pyran-4-one derivative) and the like; xanthine oxidase inhibitors such as, for example, allopurinol, oxypurinol, amflutizole, diethyldithiocarbamate, 2-styrylchromones, crisine, luteolin, kaempferol, quercetin, myricetin, isorhamnetin, benzophenones such as 2,2',4,4'-tetrahydroxybenzophenone, 3,4,5,2',3',4'hexahydroxybenzophenone and 4,4'-dihydroxybenzophenone; benzothiazinone analogs such as 2-amino-4H-1,3-benzothiazin-4-one, 2-guanidine-4H-1,3-benzothiazin-4-one and rhodanine; Nhydroxyguanidine derivative such as PR5 (1-(3,4-dimethoxy-2-chlorobenzylideneamino)-3hydroxyguanidine); 6-formylpterin and the like. The antioxidant enzymes can be released by gene therapy in the form of a viral vector and/or a non-viral vector. Suitable antioxidants are described in more detail in the literature, such as in Goodman and Gilman, The Pharmacological Basis of Therapeutics (9th Edition), McGraw-Hill, 1995; and The Merck Index on CD-ROM, Thirteenth Edition; and in STN Express, file phar and file registry. In some preferred embodiments, the antioxidants are ascorbic acid, vitamin (E, apocynin, hydralazine compounds or superoxide dismutase mimetics.

Suitable NSAIDs include but are not limited to acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indometacin, isofezolac, isoxepac, indoprofen, ketoprofen, lonazolac, loxoprofen, metiazinic acid, mofezolac, miroprofen, naproxen, oxaprozin, pirazolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetacin, burnadizone, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are more fully described in the literature, such as in Goodman and Gilman, The Pharmacological Basis of Therapeutics (9th Edition), McGraw-Hill, 1995, pages 617-657; the Merck Index on CD-ROM, 13th Edition; and in U.S. Pat. Nos. 6,057,347 and 6,297,260 issued to NitroMed Inc., the entire descriptions of which are incorporated herein as a reference. In some preferred embodiments, the NSAIDs are acetaminophen, diclofenac, flurbiprofen, ibuprofen, indometacin, ketoprofen, naproxen or aspirin.

Suitable N-methyl-D-aspartate (NMDA) receptor antagonists include but are not limited to ketamine, dextromethorphan, memantine, amantadine, nitrous oxide, gacyclidine and the like. In some preferred embodiments, the NMDA receptor antagonist is dextromethorphan.

Suitable endothelin antagonists include but are not limited to atrasentan, bosentan, darusentan, enrasentan, sitaxsentan, sulfonamide, tezosentan, BMS 193884, BQ-123, SQ 28608 and the like. Suitable endothelin antagonists are described in more detail in the literature, such as in Goodman and Gilman, The Pharmacological Basis of Therapeutics (9th Edition), McGrawHill, 1995; and The Merck Index on CD-ROM, Thirteenth Edition; and in STN Express, file phar and file registry.

Suitable immunomodulating agents include but are not limited to interferon α IIb, autologous granulocyte-macrophage colony stimulating factor, APC 8015 (Provenge), anticancer vaccines, anti-sense oligonucleotides, bacillus Calmette-Guerin (BCG) and the like.

Suitable vitamin D analogs include but are not limited to vitamin D3 analogs such as colecalciferol, calcidiol, calcitriol and the like.

In an additional aspect, the invention relates to a method for the treatment and/or prophylaxis of skin cancer which comprises, administering, to a patient who needs it, an effective amount of a compound of Formula (1), a pharmaceutically acceptable salt and solvate, isomer or prodrug thereof described herein.

In an additional aspect, the invention relates to a method for the treatment and/or prophylaxis of hematological dyscrasias, including myelodysplastic syndromes (MDSs) and for improving the efficacy of chemotherapy, radiation therapy and/or cancer immunotherapy, which comprises administering, to a patient who needs it, an effective amount of a compound of Formula (I'), a pharmaceutically acceptable salt and solvate, isomer or prodrug thereof described herein.

In another aspect, the invention relates to a method for the treatment and/or prophylaxis of cancer of an organ which comprises administering, to a patient who needs it, an effective amount of a compound of Formula (I''), a pharmaceutically acceptable salt and solvate, isomer or prodrug thereof described herein.

In another aspect, the invention relates to a method for the treatment and/or prophylaxis of fibrosis which comprises administering, to a patient who needs it, an effective amount of a compound of Formula (I'''), a pharmaceutically acceptable salt and solvate, isomer or prodrug thereof described herein.

An effective amount of at least one 2,5-dihydroxybenzene compound of Formula (I), (I'), (I'') or (I''') can be administered to the patient for example. The 2,5-dihydroxybenzene compounds and/or additional therapeutic agents can be administered separately or as components of the same composition in one or more pharmaceutically acceptable carriers.

Another aspect of the invention is that the 2,5-dihydroxybenzene derivatives of Formula (I), (I'), (I") or (I''') can optionally be used by combining them with one another. Said combinations can be in the same formulation or in formulations which will be sequentially used.

When administered separately, the 2,5-dihydroxybenzene compound of Formula (I), (I'), (I") or (I''') can be administered approximately at the same time as part of the overall treatment regimen, i.e. as a combination therapy. The expression "approximately at the same time" includes administering the 2,5-dihydroxybenzene compound simultaneously, sequentially, at the same time, at different times in the same day, on different days, as long as it is administered as part of an overall treatment regimen, i.e. a combination therapy or a therapeutic cocktail.

When administered, the compounds and compositions of the invention can be administered in combination with pharmaceutically acceptable carriers and in the dosages described herein.

When the compounds and compositions of the invention are administered as a combination of at least one 2,5-dihydroxybenzene compound of formula (I), (I'), (I") or (I''') and/or at least one additional therapeutic agent, they can also be used in combination with one or more additional compounds which are known to be effective against the specific pathology set as a treatment target. The therapeutic agents and/or the different additional compounds can be administered simultaneously with, after or before the administration of the 2,5-dihydroxybenzene compound.

In an embodiment of the invention, the 2,5-dihydroxybenzene compounds of formula (I) are administered topically, orally, buccally, parenterally, transdermally, by inhalation, rectally (for example, with the use of suppositories), intravaginally, intraocularly or otically, in unit dosage formulations containing excipients, adjuvants, and conventional, non-toxic pharmaceutically acceptable carriers, as desired.

In another embodiment of the invention, the 2,5-dihydroxybenzene compounds of formula (I') are administered topically, transdermally, orally, buccally, parenterally, by inhalation, rectally, intravaginally, intraocularly or otically, in unit dosage formulations containing excipients, adjuvants, and conventional, non-toxic pharmaceutically acceptable carriers, as desired.

In another embodiment of the invention, the 2,5-dihydroxybenzene compounds of formula (I") are administered topically, transdermically, orally, buccally, parenterally, by inhalation, rectally, intravaginally, intraocularly or otically, in unit dosage formulations containing excipients, adjuvants, and conventional, non-toxic pharmaceutically acceptable earners, as desired.

In another embodiment of the invention, the 2,5-dihydroxybenzene compounds of formula (I''') are administered topically, transdermally, orally, buccally, parenterally, by inhalation, rectally, intravaginally, intraocularly or otically, in unit dosage formulations containing excipients, adjuvants, and conventional, non-toxic pharmaceutically acceptable earners, as desired.

In a particular embodiment, 2,5-dihydroxybenzene compounds of formula (I), (I'), (I") or (I''') are administered by topical application.

The solid dosage forms for oral administration can include capsules, sustained release capsules, tablets, sustained release tablets, chewable tablets, sublingual tablets, effervescent tablets, pills, suspensions, powders, granules and gels.

The active compounds in said solid dosage forms can be mixed with at least one inert diluent such as sucrose, lactose or starch. Said dosage forms can also comprise, as in normal practice, additional substances different from the inert substances, for example, lubricants such as magnesium stearate. In the case of capsules, tablets, effervescent tablets and pills, the dosage forms can also comprise buffering agents. The soft gelatin capsules can be prepared such that they contain a mixture of the active compositions or compounds of the invention and vegetable oil. Hard gelatin capsules can contain granules of the active compound combined with a solid, powdery carner, such as lactose, sucrose, sorbitol, mannitol, potato starch, corn starch, amylopectin, cellulose derivatives and gelatin. The tablets and pills can be prepared with enteric coatings.

The liquid dosage forms for oral administration can include pharmaceutically acceptable emulsions, solutions, syrups and elixirs containing inert diluents commonly used in the art, such as water. Said compositions can also comprise adjuvants, such as wetting agents, emulsifying and suspension agents, and sweeteners, flavoring agents and perfuming agents.

Suppositories for vaginal or rectal administration of the compounds and compositions of the invention stand out among rectal and vaginal administration forms; such suppositories can be prepared by mixing the compounds or compositions with a suitable non-irritating excipient such as cocoa butter and polyethyleneglycols which are solid at room temperature but liquid at rectal temperature, such that they will melt in the rectum and vagina and release the compounds and compositions.

The injectable preparations, for example, injectable and sterile aqueous or oily suspensions can be formulated according to the known art using suitable dispersing agents, wetting agents and/or suspension agents. The sterile injectable preparation can also be a sterile injectable solution or suspension in a non-toxic, parenterally acceptable diluent or solvent, for example, a solution in 1,3-butanediol. Included among the acceptable carriers and solvents which can be used are water, Ringer solution, and isotonic sodium chloride solution. The sterile fixed oils are also conventionally used as solvents or suspension mediums.

The topical administration of the compounds and compositions of the invention can be in the form of creams, gels, lotions, liquids, ointments, spray solutions, sprays, solid bars, emulsions, microemulsions and the like which can be formulated according to the conventional methods using suitable excipients, such as, for example, emulsifying agents, surfactants, thickeners, sun protection agents, wetting agents, cooling agents, skin relaxing agents, skin conditioning agents, skin protectors, emollients, wetting agents, dyes and combinations of two or more of them.

The compounds and compositions of the invention can be administered by transdermal route in the form of transdermal patches or iontophoresis devices. Other components can optionally be incorporated in the transdermal patches. For example, compositions and/or transdermal patches can be formulated with one or more preservatives or bacteriostatic agents including but not limited to methyl hydroxybenzoate, propyl hydroxybenzoate, chlorocresol, benzalkonium chloride and the like. Fabric pads or balls of a bandage-type material, for example gauze, can be impregnated with the compositions in solution, lotion, cream, ointments or other form which can also be used for topical application. In an embodiment, the compositions of the invention are administered in the form of a transdermal patch. In another embodiment, the compositions of the invention are administered in the form of a sustained release transdermal patch. The transdermal patches of the invention can include any conventional form such as, for example, an adhesive matrix, a polymeric matrix, a patch with a deposit, a matrix-type or monolithic laminated structure, and they are generally formed by one or more reinforcing layers, adhesives, penetration enhancers, an optional membrane controlling the rate, and a release coating which is removed to expose the adhesives before the application. The polymeric matrix patches also comprise a material forming a polymeric matrix. Suitable transdermal patches are described in more detail in, for example, U.S. Pat. Nos. 5,262,165, 5,948,433, 6,010,715 and 6,071,531, the entire descriptions of which are incorporated herein.

The compositions of this invention can additionally include conventional excipients, i.e. pharmaceutically acceptable organic or inorganic substance carriers, suitable for the parenteral application that do not dangerously react with the active compounds. Suitable pharmaceutically acceptable carriers include, for example, water, saline solutions, alcohol, vegetable oils, polyethyleneglycols, gelatin, lactose, amylose, magnesium stearate, talc, surfactants, silicic acid, viscous paraffin, perfuming oil, monoglycerides and diglycerides of fatty acids, petroethral fatty acid esters, hydroxymethylcellulose, polyvinylpyrrolidone and the like. The pharmaceutical preparations can be sterilized and, if desired, mixed with auxiliary agents, for example, lubricants, preservatives, stabilizers, wetting agents, emulsifying agents, salts for affecting osmotic pressure, buffers, dyes, flavoring agents and/or aromatic substances and the like which do not dangerously react with the active compounds. For parenteral application, the particularly suitable carriers consist of preferably oily or aqueous solutions, as well as suspensions, emulsions or implants. The aqueous suspensions can contain substances which increase the viscosity of the suspension and include, for example, sodium carboxymethylcellulose, sorbitol and/or dextran. The suspension can also optionally contain stabilizers.

If desired, the composition can also contain minor amounts of wetting agents, emulsifying agents and/or pH buffering agents. The composition can be a liquid solution, suspension, emulsion, tablet, pill, capsule, sustained release formulation or powder. The composition can be formulated as a suppository, with traditional binding agents and carriers such as triglycerides.

The oral formulations can include conventional carriers such as pharmaceutical grade mannitol, lactose, starch, magnesium stearate, sodium saccharine, cellulose, magnesium carbonate and the like.

Different delivery systems are known and can be used to administer the compounds or compositions of the invention, including, for example, encapsulation in liposomes, microbubbles, emulsions, microparticles, microcapsules and the like. The required dosage can be administered in single unit form or in sustained release form.

The suitable sustained release forms as well as the materials and methods for their preparation are described in, for example, "Modified-Release Drug Delivery Technology", Rathbone, M. J. Hadgraft, J. and Roberts, M. S. (eds.), Marcel Dekker, Inc., New York (2002); "Handbook of Pharmaceutical Controlled Release Technology", Wise, D. L. (ed.), Marcel Dekker, Inc. New York, (2000); "Controlled Drug Delivery", vol. I, Basic Concepts, Bruck, S. D. (ed.), CRC Press Inc., Boca Raton (1983) and of Takada, K. and Yoshikawa, H., "Oral Drug delivery", Encyclopedia of Controlled Drug Delivery, Mathiowitz, E. (ed.), John Wiley & Sons, Inc., New York (1999), vol. 2, 728-742; Fix, J., "Oral drug delivery, small intestine and colon", Encyclopedia of Controlled Drug Delivery, Mathiowitz, E. (ed.), John Wiley & Sons, Inc., New York (1999), vol. 2, 698-728; the entire descriptions of which are incorporated herein as a reference.

In an embodiment of the invention, the oral administration form of the compounds of 2,5-dihydroxybenzene is in a sustained release form additionally comprising at least one coating or matrix. The sustained release coating or matrix includes but is not limited to natural, semisynthetic or synthetic polymers insoluble in water, modified polymers, waxes, fats, fatty alcohols, fatty acids, natural, semi-synthetic or synthetic plasticizers, or a combination of two or more of them.

Suitable polymers insoluble in water include but are not limited to acrylic resins such as, for example, poly(meth)acrylates, polyalkyl($C_{i\_4}$)-(meth)acrylates, polydialkyl($C_{i\_4}$)aminoalkyl($C_{i\_4}$)-(meth)acrylates and/or copolymers and the like, and combinations of two or more of them; of ethyl acrylate and methyl methacrylate copolymers with a 2:1 molar monomer ratio (EUDRAGIT NE30D®), ethyl acrylate, methyl methacrylate and triethylammonium ethyl methacrylate chloride copolymers with a 1:2:0.1 molar monomer ratio (EUDRAGIT RS®), ethyl acrylate, methyl methacrylate and triethylammonium ethyl methacrylate chloride copolymers with a 1:2:0.2 molar monomer ratio (EUDRAGIT RL®) and the like, and combinations of two or more of them.

Suitable polymers insoluble in water include but are not limited to cellulose derivatives, such as, for example, alkylcelluloses, ethylcellulose, cellulose esters, cellulose acetate, AQUACOAT®, SURELEASE® and the like.

Suitable natural, semisynthetic or synthetic waxes, fats or fatty alcohols include but are not limited to carnauba wax, beeswax, glycerol monostearate, glycerol monobehenate, glycerol ditripalmitostearate, microcrystalline wax, cetyl alcohol, cetylstearyl alcohol and the like, and combinations of two or more of them.

Suitable plasticizers include but are not limited to lipophilic diesters of an aliphatic or aromatic C6-C40 dicarboxylic acid, Ci-CS aliphatic alcohols, such as, for example, dibutyl phthalate, diethyl phthalate, dibutyl sebacate, diethyl sebacate and the like; hydrophilic or lipophilic citric acid esters, such as, for example, triethyl citrate, tributyl citrate, acetyltributyl citrate, acetyltriethyl citrate and the like; polyethyleneglycols, propyleneglycols, glycerol esters, such as, for example, triacetine, MYVACET® (acetylated mono and diglycerides, $C_{23}H_{44}O_5$ to $C_{25}H_{47}O$), triglycerides of medium chain length (MIGLYOL®), oleic acid or mixtures of at least two of said plasticizers. The sustained release formulations can comprise one or more plasticizers in amounts of approximately 5 to approximately 50% by weight, based on the amount of polymer(s) used.

The sustained release formulations can also comprise other conventional excipients known by persons skilled in the art, such as, for example, lubricants, colored pigments, surfactants and the like. The sustained release formulations can also contain an enteric coating, such that they are gastroresistant.

Suitable enteric coatings include but are not limited to methacrylic acid/methyl methacrylate copolymers with a 1:1 molar monomer ratio (EUDRAGIT L®), methacrylic acid/methyl methacrylate copolymers with a 1:2 molar monomer ratio (EUDRAGIT S®), methacrylic acid/ethyl acrylate copolymers with a 1:1 molar monomer ratio (EUDRAGIT 30D55®), methacrylic acid/methyl acrylate/methyl methacrylate copolymers with a 7:3:1 molar monomer ratio (EUDRAGIT FS®), shellac, hydroxypropylmethylcellulose, acetate-succinates, cellulose acetate-phthalates or a combination of two or more of them. These enteric coatings can also be optionally used in combination with the water-insoluble poly(meth)acrylates described herein. In one embodiment, the enteric coatings are used in combination with EUDRAGIT NE30D® and/or EUDRAGIT RL® and/or EUDRAGIT RS®.

The enteric coatings can be applied using conventional processes known by persons skilled in the art, as described in, for example, Johnson, 1. L., "Pharmaceutical tablet coating", Coatings Technology Handbook (Second Edition), Satas, D. and Tracton, A. A. (eds), Marcel Dekker, Inc. New York, (2001), 863-866; Carstensen, T., "Coating Tablets in Advanced Pharmaceutical Solids", Swarbrick, 1. (ed.), Marcel Dekker, Inc. New York (2001), 455-468; Leopold, C. S., "Coated dosage forms for colon-specific drug delivery", Pharmaceutical Science & Technology Today, 2 (5), 197-204 (1999), Rhodes, C. T. and Porter, S. c., Coatings, in Encyclopedia of Controlled Drug Delivery. Mathiowitz, E. (ed.), John Wiley & Sons, Inc., New York (1999), vol. 1, 299-311; the entire descriptions of which are incorporated herein as a reference.

In one embodiment of the invention, the sustained release formulations comprising at least one 2,5-dihydroxybenzene compound of the invention are in an immediate release form and in a sustained release form in the same formulation. The formulation can additionally comprise at least one additional therapeutic agent, such as, for example, chemotherapeutic agents, steroids, retinoids, antimicrobial compounds, antioxidants, anti-inflammatory compounds, and combinations of two or more of them.

Although individual needs may vary, the determination of the optimal ranges for effective amounts of the compounds and/or compositions is part of the common experience of persons skilled in the art. Generally, the necessary dosage for providing an effective amount of the compounds and compositions, which can be adjusted by a person skilled in the art, will vary depending on age, health, physical condition, gender, diet, weight, degree of the disorder of the receptor, treatment frequency and nature and scope of the disorder or disease, medical condition of the patient, the administration route, pharmacological considerations such as activity, efficacy, pharmacokinetic profile and of toxicology of the particular compound used, if a drug delivery system is used, and if the compound is administered as part of a combination of drugs.

The amount of a given 2,5-dihydroxybenzene compound that will be effective in treating a particular disorder or condition will depend on the nature of the disorder or condition, and can be determined by conventional clinical techniques, including the reference to Goodman and Gilman, above; The Physician's Desk Reference, Medical Economics Company, Inc., Oradell, N.J., 1995; and Drug Facts and Comparisons, Inc., St. Louis, Mo., 1993; the entire descriptions of which are incorporated herein as a reference. The exact dose to be used in the formulation will also depend on the administration route and the severity of the disease or disorder, and must be chosen by the physician and in accordance with the patient's circumstances.

The duration of treatment will typically depend on the particular condition, its severity, the condition of the patient, and the like, and will readily be determined by one of skill in the art. Illustrative courses of therapy include 1 week, 2 weeks, 3 weeks, 4 weeks, 5 weeks, 6 weeks, 7 weeks, 8 weeks, 9 weeks, 10 weeks, 11 weeks, 12 weeks, 3.5 months, 4 months, 4.5 months, 5 months, 6 months, 9 months, a year, or longer as needed.

In treating a subject suffering from a disorder described herein, treatment may be continued until at least a 10% improvement is effected in a symptom associated with the condition. In other embodiments, treatment is continued until the subject in need of such treatment experiences an improvement of at least about 20%, at least about 30%, at least about 40%, preferably at least about 50%, preferably at least about 60%, more preferably at least about 70%, more preferably at least about 80%, even more preferably 90% or greater in a symptom associated with a disorder described herein.

In a particular embodiment of the invention, a compound of formula (I), (I'), (I") or (I''') is administered at least once per week. In other embodiments, a compound of formula (I), (I'), (I") or (I''') is administered at least once per day. In yet other embodiments, a compound of formula (I), (I'), (I") or (I''') is administered twice per day. In another particular embodiment, a compound of formula (I), (I'), (I") or (I''') is administered over a period of at least about one week. In other embodiments, a compound of formula (I), (I'), (I") or (I''') is administered over a period of at least about four weeks.

Therapeutic amounts can be empirically determined and will vary with the particular condition being treated, the subject, the particular formulation components, dosage form, and the like.

In a particular embodiment, a compound of formula (I), (I'), (I") or (I''') is present in a pharmaceutical composition in an amount of at least about 1% w/w. In other embodiments, a compound of formula (I), (I'), (I") or (I''') is present in a pharmaceutical composition in an amount of at least about 2.5% w/w, at least about 5% w/w, at least about 10% w/w, or at least about 15% w/w.

In one embodiment, the 2,5-dihydroxybenzene compounds of Formula (I), (I'), (I") or (I''') can be administered by transdermal, oral, buccal, parenteral, rectal or intravaginal, intraocular or otical route or by inhalation in an amount of approximately 0.05 g a day to approximately 50 g a day. In particular embodiments, the 2,5-dihydroxybenzene compounds of Formula (I), (I'), (I") or (I''') can be administered by transdermal, oral, buccal, parenteral, rectal or intravaginal, intraocular or otical route or by inhalation in an amount of approximately 0.10 g a day to approximately 25 g a day. In more particular embodiments, the 2,5-dihydroxybenzene compounds of Formula (I), (I'), (I") or (I''') can be administered by transdermal, oral, buccal, parenteral, rectal or intravaginal, intraocular or otical route or by inhalation in an amount of approximately 0.25 g a day to approximately 109 a day. In a more particular embodiment, the 2,5-dihydroxybenzene compounds of Formula (I), (I'), (I") or (I''') can be administered in an amount of approximately 0.5 g a day to approximately 5 g a day. In an even more particular embodiment, the 2,5-dihydroxybenzene compounds of Formula (I), (I'), (I") or (I''') can be administered in an amount of approximately 0.75 g a day to approximately 2.5 g a day. In another particular embodiment, the 2,5-dihydroxybenzene compounds of Formula (I), (I'), (I") or (I''') can be administered in an amount of approximately 1 g a day to approximately 1.5 g a day. The particular amounts of the 2,5-dihydroxybenzene compounds of Formula can be administered in the form of a single dose once a day; or in multiple doses several times throughout the entire day; or as a sustained release oral Formulation. In one embodiment of the invention, approximately 50 g, 25 g, 10 g, 5 g, 1 g, 0.75 g, 0.5 g, 0.25 g or 0.1 g of the 2,5-dihydroxybenzene compounds of Formula (I), (I'), (I") or (I''') are, administered once a day (q.d) by transdermal, oral, buccal, parenteral, rectal or intravaginal, intraocular or otical route or by inhalation. In another embodiment of the invention, approximately 50 g, 25 g, 109, 5 g, 1 g, 0.75 g, 0.5 g, 0.25 g or 0.1 g of the 2,5-dihydroxybenzene compounds of Formula (I), (I'), (I") or (I''') are administered twice a day (hj.d) by transdermal, oral, buccal, parenteral, rectal or intravaginal, intraocular or otical route or by inhalation. In another embodiment of the invention, approximately 50 g, 25 g, 10 g, 5 g, 1 g, 0.75 g, 0.5 g, 0.25 g or 0.1 g of the 2,5-dihydroxybenzene compounds of Formula (I), (I'), (I") or (I"') are administered three times a day (ti.d.) by transdermal, oral, buccal, parenteral, rectal or intravaginal, intraocular or otical route or by inhalation. In another embodiment of the invention, approximately 50 g, 25 g, 109, 5 g, 1 g, 0.75 g, 0.5 g, 0.25 g or 0.1 g of the 2,5-dihydroxybenzene compounds of Formula (I), (I'), (I") or (I"') are administered four times a day by transdermal, oral, buccal, parenteral, rectal or intravaginal, intraocular or otical route or by inhalation.

In particular embodiments, the compounds of 2,5-dihydroxybenzene of Formula (I), (I'), (I") or (I"') can be administered by topical route in a Formulation comprising an amount of approximately 0.001% to approximately 30% (w/w) of the 2,5-dihydroxybenzene compounds of Formula (I), (I'), (I") or (I"'). In a more particular embodiment, the 2,5-dihydroxybenzene compounds of Formula (I), (I'), (I") or (I"') can be administered by topical route in a Formulation comprising an amount of approximately 0.01% to approximately 20% (w/w) of the 2,5-dihydroxybenzene compounds of Formula (I), (I'), (I") or (I"'). In an even more particular embodiment, the 2,5-dihydroxybenzene compounds of Formula (I), (I'), (I") or (I"') can be administered by topical route in a formulation comprising an amount of approximately 0.1% to approximately 15% (w/w) of the 2,5-dihydroxybenzene compounds of Formula (I), (I'), (I") or (I"'). In a more particular embodiment, the 2,5-dihydroxybenzene compounds of Formula (I), (I'), (I") or (I"') can be administered by topical route in a formulation comprising an amount of approximately 0.5% to approximately 10% (w/w) of the 2,5-dihydroxybenzene compounds of Formula (I), (I'), (I") or (I"'). In another particular embodiment, the 2,5-dihydroxybenzene compounds of Formula (I), (I'), (I") or (I"') can be administered by topical route in a formulation comprising an amount of approximately 1% to approximately 5% (w/w) of the 2,5-dihydroxybenzene compounds of Formula (I), (I') or (I"). In a more particular embodiment, the 2,5-dihydroxybenzene compounds of Formula (I) can be administered by topical route in a formulation comprising an amount of approximately 2.5% to approximately 4% (w/w) of the 2,5-dihydroxybenzene compounds of Formula (I), (I'), (I") or (I"'). The topical formulation comprising the 2,5-dihydroxybenzene compounds of Formula (I), (I'), (I") or (I"') can be administered in the form of a single dose once a day; or in multiple doses several times throughout the entire day. In an embodiment of the invention, the topical formulation comprising approximately 30%, 20%, 15%, 10%, 5%, 2.5%, 1%, 0.5%, 0.1% or 0.001% of the 2,5-dihydroxybenzene compounds of Formula (I), (I'), (I") or (I"') is administered four times a day.

In another embodiment of the invention, the topical formulation comprising approximately 30%, 20%, 15%, 10%, 5%, 2.5%, 1%, 0.5%, 0.1% or 0.001% of the 2,5-dihydroxybenzene compounds of Formula (I), (I'), (I") or (I"') is administered three times a day.

In yet another embodiment of the invention, the topical formulation comprising approximately 30%, 20%, 15%, 10%, 5%, 2.5%, 1%, 0.5%, 0.1% or 0.001% of the 2,5-dihydroxybenzene compounds of Formula (I), (I'), (I") or (I"') is administered twice a day (hj.d).

In another embodiment of the invention, the topical formulation comprising approximately 30%, 20%, 15%, 10%, 5%, 2.5%, 1%, 0.5%, 0.1% or 0.001% of the 2,5-dihydroxybenzene compounds of Formula (I), (I'), (I") or (I"') is administered once a day.

In yet other embodiments, the invention provides a kit or package comprising a compound of Formula (I), (I'), (I") or (I"'), in packaged form, accompanied by instructions for use. The compound of formula (I), (I'), (I") or (I"') may be packaged in any manner suitable for administration, so long as the packaging, when considered along with the instructions for administration, indicates the manner in which the compound of formula (I), (I'), (I") or (I"') is to be administered.

For example, a kit may comprise a compound of formula (I), (I'), (I") or (I"') in unit dosage form, along with instructions for use. For example, such instructions may indicate that administration of a compound of formula (I), (I'), (I") or (I"') is useful in the treatment of basal cell carcinoma. The compound of formula (I), (I'), (I") or (I"') may be packaged in any manner suitable for administration. For example, when the compound of formula (I), (I'), (I") or (I"') is in oral dosage form, e.g., is in the form of a coated tablet, then the kit may comprise a sealed container of coated tablets, blister strips containing the tablets, or the like.

Various embodiments according to the above may be readily envisioned, and would depend upon the particular dosage form, recommended dosage, intended patient population, and the like.

The packaging may be in any form commonly employed for the packaging of pharmaceuticals, and may utilize any of a number of features such as different colors, wrapping, tamper-resistant packaging, blister packs or strips, and the like.

EXAMPLES

The following non-limiting examples additionally describe and enable a person skilled in the art to prepare and use the present invention.

Example 1

Effect of 2,5-Dihydroxybenzoate on Fibrosis

Sterile gelatin sponges (1 mm$^3$; Curaspon Dental, Clinimed Holding, Zwanenburg, The Netherlands) were subcutaneously implanted in the dorsal region of the neck in Sprague-Dawley rats after the induction of intraperitoneal anesthesia. The animals were split into two groups: group A, the sponges were moistened with 200 III of saline solution which contained 25 µg/ml of heparin and 10 µg/ml of basic FGF (bFGF); group B, the sponges were moistened in the same solution as in group A, but which solution further contained 2,5-dihydroxybenzoate (100 µM). After 7 days, the sponges and the surrounding subcutaneous fat were removed and histologically analyzed. The septa of connective tissue (fibroblasts, collagen fibers and elastic fibers) separating the adipose lobules from one another were analyzed to demonstrate the antifibrotic effect of 2,5-dihydroxybenzoate.

Figure 1:
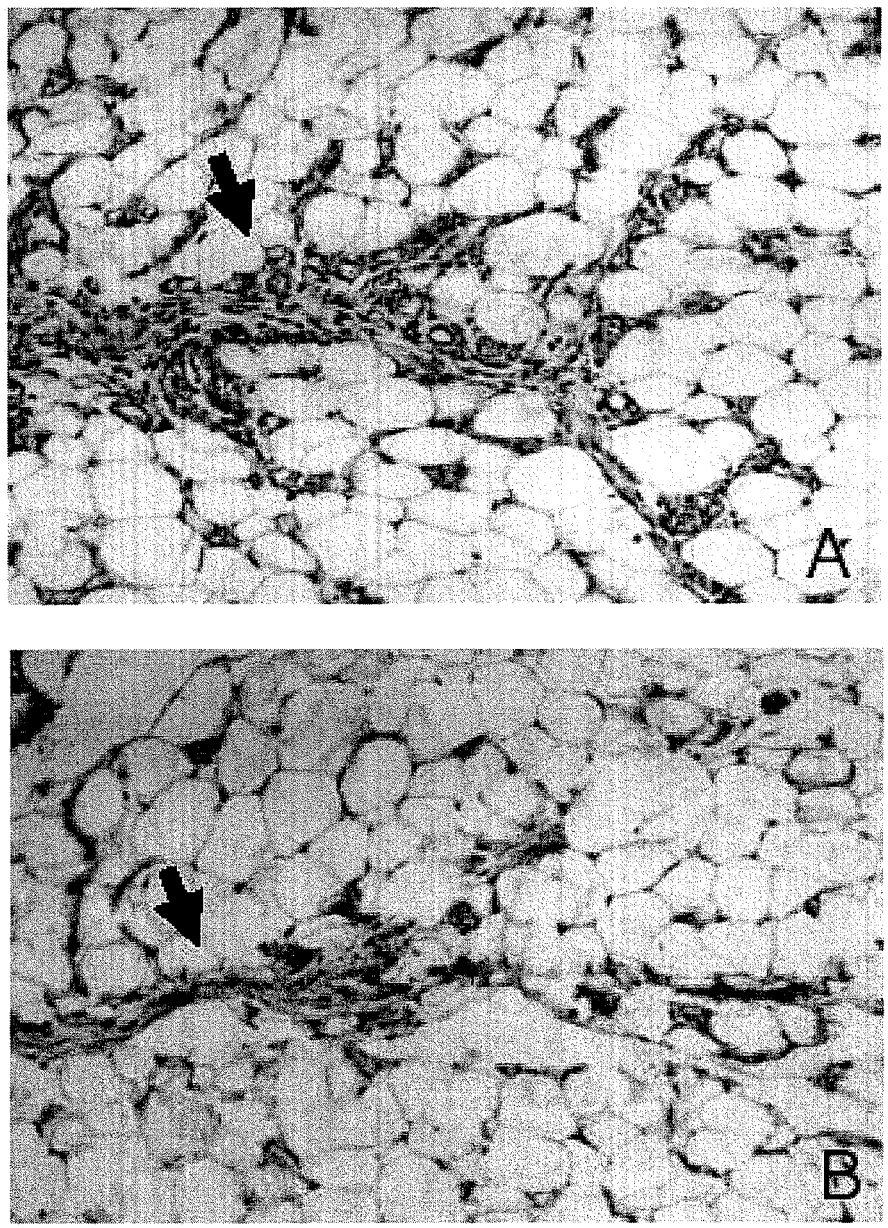
FIG. 1 shows the fibrosis induced in rat adipose tissue upon subcutaneously implanting a gelatin sponge containing only basic fibroblast growth factor (bFGF) (Figure A) or containing bFGF plus 2,5-dihydroxybenzoate (Figure B) for 7 days.

The combined application of bFGF and 2,5-dihydroxybenzoate in the gelatin sponges reduces bFGF-induced fibrosis, since the septa of connective tissue in the adipose tissue contain fewer fibroblasts when 2,5-dihydroxybenzoate is present, as is shown in the comparison between FIG. 1A and FIG. 1B.

These data support the use of 2,5-dihydroxybenzene compounds for treating both local and general fibrotic processes.

Example 2

2,5-Dihydroxybenzoate Inhibits Glioma Cell Proliferation

The following example shows the efficacy of 2,5-dihydroxybenzoate to reduce the proliferative capacity of glioma cells and supports the use of the compound in treating gliomas.

The cell line used was rat glioma C6 cells. The cells were cultured as previously described (Cuevas P et al. *Neural Res*, 2005). The cells were cultured as adherent cells in Dulbecco's modified Eagle's medium, supplemented with 7.5% (v/v) of fetal bovine serum, 10 μg/ml of streptomycin and 10 units/ml of penicillin. The tumor cells were seeded in 24-well plates at a density of 10,000 cells/well, and were incubated at 37° C. in a humidified chamber with 5% $CO_2$. Once adhered, the cells were treated or not (controls) with 2,5-dihydroxybenzoate at 100, 200, 500 or 1000 μM and they were allowed to proliferate for 48 h. After this time the glioma cell proliferation was evaluated by means of staining the fixed cells with crystal violet. The number of cells is proportional to the amount of retained dye, which was spectrophotometrically determined by measuring the absorbance at 595 nm once the dye was extracted from the cells.

Figure 2:
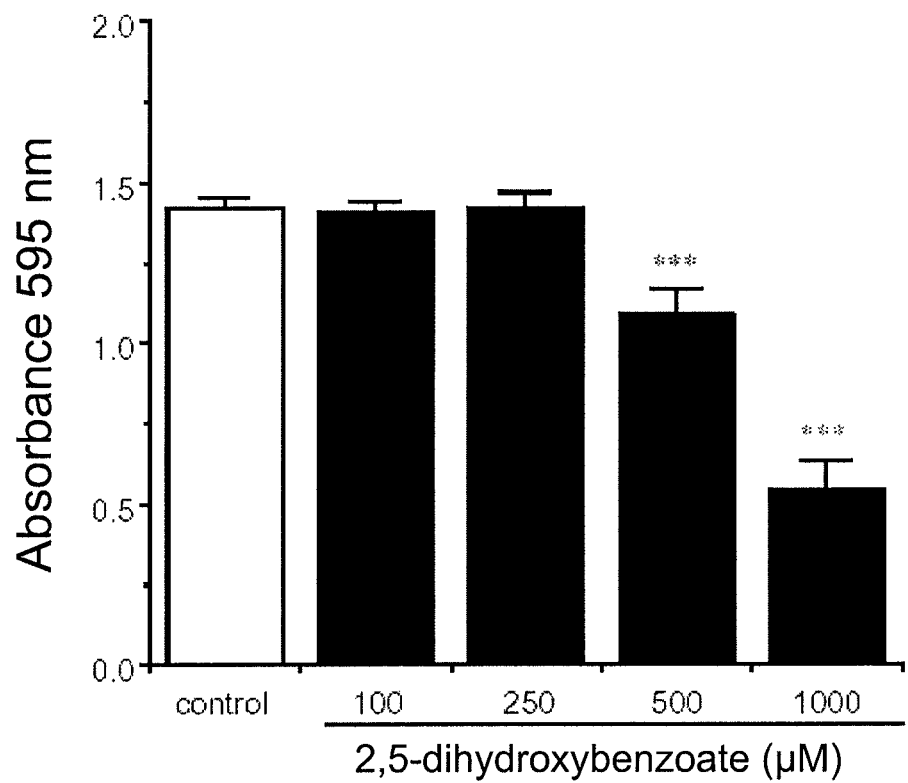
FIG. 2 shows the effect of the treatment with potassium 2,5-dihydroxybenzoate (gentisic acid) on the proliferation of rat glioma C6 cells. 2,5-dihydroxybenzoate was administered or not administered (control) after seeding the C6 cells in 24-well plates ($10^4$ per well) until their fixing after 48 hours. The data are expressed as mean±SEM of the absorbance at 595 nm, which is proportional to the number of cells stained with crystal violet. The data were obtained from 3 cultures for each treatment. The white bar represents the value of the control cells, whereas the black bars show the value in the presence of 2,5-dihydroxybenzoate (100, 200, 500 and 1000 ~M). *** indicates $p<0.001$ with respect to the control by means of a single factor analysis of variance (ANOYA) followed by a Student-Newman-Keuls post-analysis.

Treatment with 2,5-dihydroxybenzoate inhibited rat glioma C6 cell proliferation in a concentration-dependent manner, an effect which was statistically significant at the concentrations of 500 and 1000 μM (FIG. 2).

Example 3

Effect of 2,5-Dihydroxycinnamic Acid on Rat Glioma C6 Cell Proliferation

The following example shows the efficacy of 2,5-dihydroxycinnamic acid (3-(2,5-dihydroxyphenyl)-2-propenoic acid; 2,5-DHC) to reduce the proliferative capacity of glioma cells and supports the use of the compound in treating gliomas.

Figure 3:
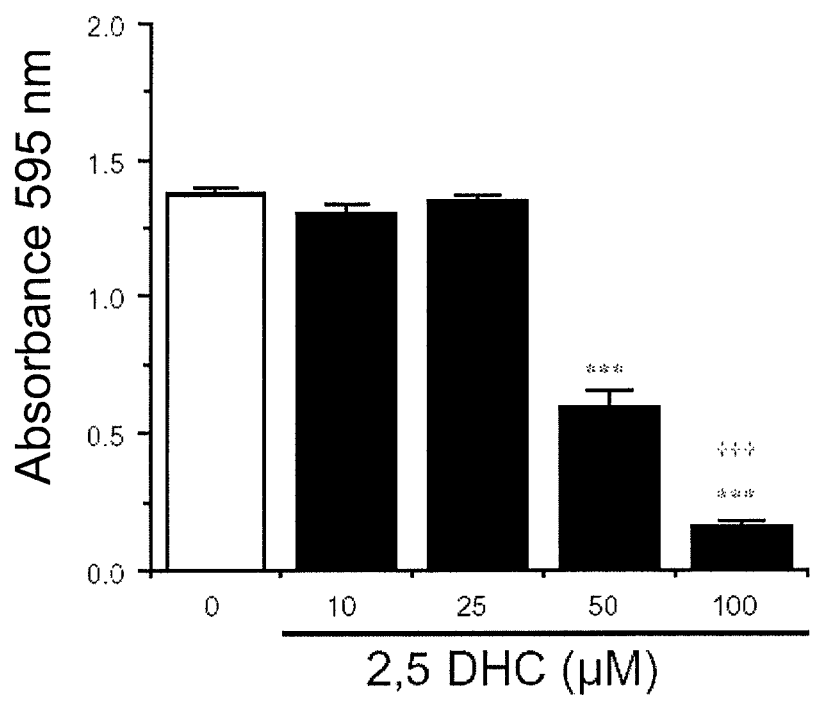
FIG. 3 shows the effect of the treatment with 3-(2,5-dihydroxyphenyl)-2-propenoic acid (2,5-dihydroxycinnamic acid; 2,5-DHC, 10-100 µM) on the proliferation of rat glioma C6 cells. 2,5-DHC was administered or not administered (control) after seeding the C6 cells in 24-well plates ($10^4$ per well) until their fixing after 48 hours. The data are expressed as the mean±SEM of the absorbance at 595 nm, which is proportional to the number of cells stained with crystal violet. The data were obtained from 3 cultures for each treatment. The white bar represents the value of the control cells, whereas the black bars show the values in the presence of 2,5-DHC (10, 25, 50 and 100 µM). *** indicates $p<0.001$ with respect to the control by means of a single-factor analysis of variance (ANOYA) followed by a Student-Newman-Keuls postanalysis.

The cell line used was the C6 cell line and the experiment was carried out as described in Example 2. Once adhered, the cells were treated or not (controls) with increasing concentrations of 2,5-DHC (10, 25, 50 and 100 μM) and they were allowed to proliferate for 48 h. After this time the glioma cell proliferation was evaluated by means of staining the fixed cells with crystal violet. The number of cells is proportional to the amount of retained dye, which was determined spectrophotometrically by measuring absorbance at 595 nm once the dye was extracted from the cells. The 2,5-DHC, at the concentration of 50 μM reduced the C6 cell proliferation to less than half, while proliferation was reduced to one tenth in the presence of 100 μM of 2,5-DHC (FIG. 3).

Example 4

Effects of 2,5-Dihydroxybenzene Sulfonate and 2,5-Diacetoxybenzene Sulfonate on Progression of Subcutaneous Gliomas Already Established in Rats Rat C6 glioma cells were cultured as previously described (Cuevas P et al. *Neural Res*, 2005). The C6 cells cultured to confluence in 75 $cm^2$ flasks were removed and implanted under the abdominal skin in anesthetized rats. The existence of a tumor in the implantation area was observed five days after the implantation of the tumor cells. Only the rats in which the existence of a tumor was observed were randomly assigned to be treated with daily intraperitoneal injections of 2,5-dihydroxybenzene sulfonate (DHBS; 100 mg/kg/day), 2,5-diacetoxybenzene sulfonate (DABS; 100 mg/kg/day) or the carrier (0.9% NaCl). After 10 days of treatment, the subcutaneous gliomas were removed and their volume was calculated according to the formula $V=4/3\pi \cdot (L/2) \cdot (A/2)^2$ (in $mm^3$) where L is the larger diameter and A is the smaller diameter, both expressed in mm.

Figure 4:
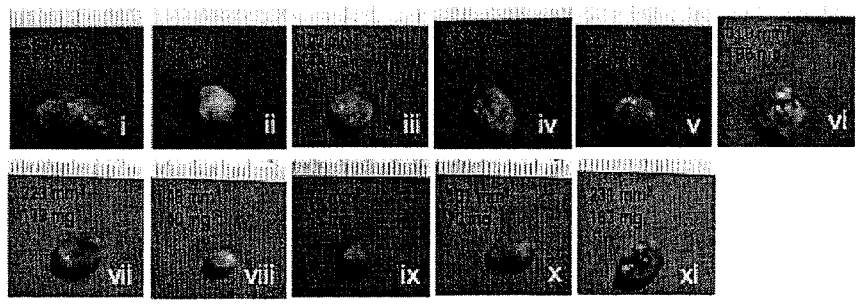
FIG. 4 shows the effect of the intraperitoneal administration of potassium 2,5-dihydroxibenzene sulfonate (DHBS) and potassium 2,5-diacetoxybenzene sulfonate (DABS) on the progression of tumors established in rats after the subcutaneous implantation of rat glioma C6 cells ($5\times10^5$ C6 cells). The upper rows show the tumors developed in rats treated with carrier (0.9% NaCl) (i to xi), the intermediate rows show the tumors developed in rats treated with DHBS (i.p.; 100 mg/kg/day for 10 days) (xii to xxiii), whereas the bottom row shows the tumors or the absence thereof (indicated by N.D.) in rats treated with DABS (i.p.; 100 mg/kg/day for 10 days) (xxiv to xxxvi). The tumors were removed 10 days after the start of the treatment, which started once the presence of a tumor was verified on the fifth day after the implantation of glioma cells.
Figure 4:
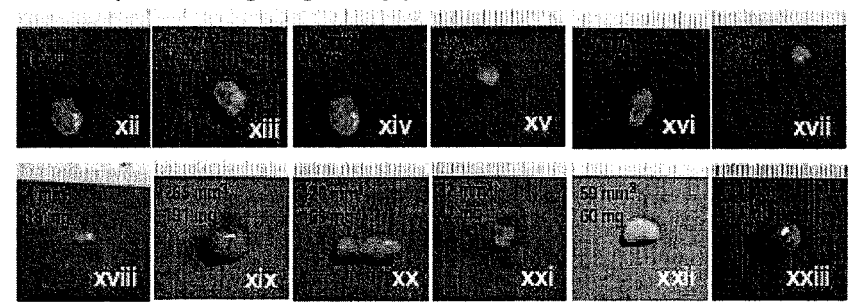
Figure 4:
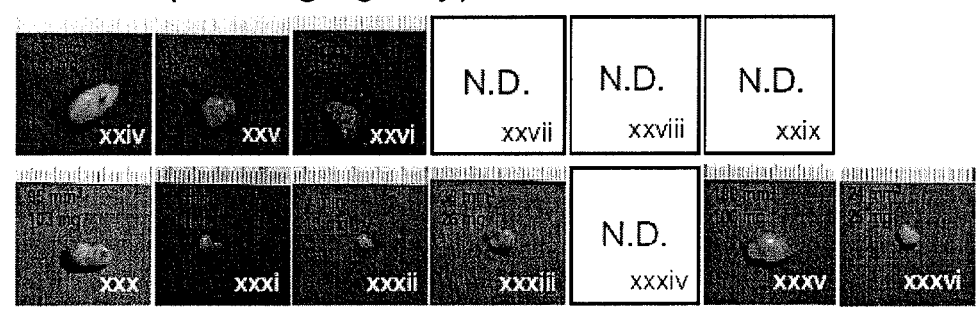
Figure 5:
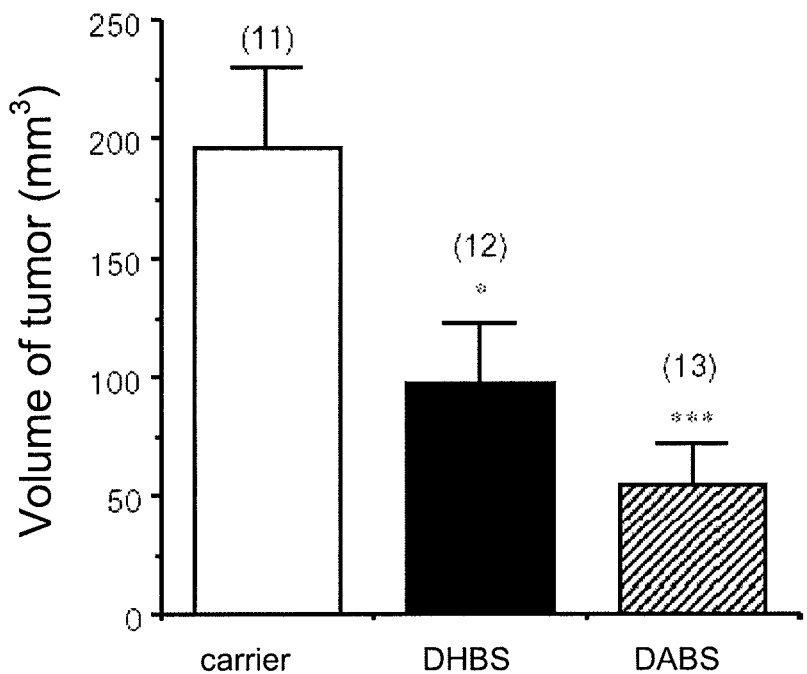
FIG. 5, Part A, shows the comparison of the volumes of the tumors developed in rats treated intraperitoneally with carrier (0.9% NaCl) (white bar), potassium 2,5-dihydroxibenzene sulfonate (DHBS; 100 mg/kg/day) (black bar) or potassium 2,5-diacetoxybenzene sulfonate (DABS; 100 mg/kg/day) (striped bar) for 10 days. The data are expressed as the mean±SEM of the tumor volume of the rats of each group. The number of rats of each group is indicated in brackets.

In general terms, the size of the tumors obtained from the rats treated with the carrier was greater than that of those obtained from the rats treated with DHBS or DABS (FIG. 4). Actually, the average size of the subcutaneous gliomas obtained from the rats treated with DHBS was less than that of the rats treated with carrier, and this average volume was even less in the rats treated with DABS (FIG. 5A). Furthermore, in the group of rats treated with DABS, despite the fact that all the rats had established tumors prior to treatment, 4 rats were tumor-free when treatment ended. In fact, a statistical probability analysis ($\chi^2$ test) showed that there is a greater probability of being tumor-free in the group treated with DABS than in the group treated with DHBS (FIG. 5B).

This example demonstrates the inhibitory effect of 2,5-dihydroxybenzene sulfonate on the progression of already established heterotopic gliomas and that the administration of 2,5-acetoxybenzene sulfonate represents a significant advantage over the administration of 2,5-dihydroxybenzene sulfonate on the treatment of these tumors.

Example 5

Effect of 2,5-Diacetoxybenzene Sulfonate on Apoptosis of Subcutaneous Gliomas Already Established in Rats Tumor cells elude the programmed cell death process or apoptosis that normal cells experience. Apoptosis induction in tumor cells is one way to confront the development of a tumor. To evaluate the effect of potassium 2,5-dihydroxybenzene sulfonate (DABS) on tumor cell apoptosis, 6). 1 m thick sections of the subcutaneous gliomas described in example 4 were made. The sections were stained with hematoxylin and eosin and observed at a magnification of 313 times using immersion oil. In these conditions, cell apoptosis is shown by the existence of apoptotic bodies appearing as strongly chromogenic granules in the cell nucleus which is frequently fragmented. As can be seen in FIG. 6A, the presence of tumor cells in the process of apoptosis is very scarce in the gliomas obtained from rats treated only with the carrier. However, a large number of tumor cells in apoptosis can be observed in the tumors from rats treated with DABS (100 mg/kg/day) for 10 days (FIG. 6B).

This example shows the treatment capacity of DABS to promote apoptosis in tumor cells of already established subcutaneous gliomas, a property which definitely contributes to the inhibitory effect of treatment with DABS on the growth of these tumors shown in the previous example.

Example 6

Effect of 2,5-Diacetoxybenzene Sulfonate on Human Tumor Cell Proliferation

The cell lines used were the human prostate cancer PC-3 cells and human lung cancer A549 cells. 2000 cells were seeded per well in 96-well plates and they were allowed to adhere overnight. Then the cells were treated or not (controls) with potassium 2,5-diacetoxybenzene sulfonate (DABS) (1-200 μM) and they were allowed to proliferate for 96 h. After this time, the PC-3 and A549 cell proliferation was evaluated by determining the final number of cells by means of the viability method of yellow tetrazolium salt (XTT). The data were expressed as a percentage of the control (without treatment). As can be seen in FIG. 7, DABS caused a significant inhibition of human prostate cancer and lung cancer cell proliferation.

Example 7

Effect of 2,5-Diacetoxybenzene Sulfonate on the Progression of Subcutaneous Tumors in a Prostate Cancer Cell Implantation Model in Athymic Mice $5 \times 10^6$ human prostate cancer PC-3 cells were subcutaneously injected in male athymic mice (Nu/Nu) of 6-8 weeks of age and weighing 20-26 g. Ten days after the implantation of the tumor cells, the mice were randomly split into two groups: one of them received a daily injection of potassium 2,5-diacetoxybenzene sulfonate (DABS) by intraperitoneal route at a dose of 100 mg/kg dissolved in saline (0.9% NaCl) whereas the other group received a daily injection of carrier (saline). The treatments were administered for 15 days. The volumes of the tumors induced by the implantation of PC-3 cells were measured through the skin on alternating days using a Vernier caliper. The volume was calculated using the formula $V=(D \times 2d)/2$, where D is the larger diameter in mm, d is the smaller diameter in mm and V is the volume in $mm^3$. At the end of treatment, the mice were sacrificed and the tumors were weighed. As can be seen in FIG. 8A, treatment with DABS significantly reduced the human prostate cell tumor growth in athymic mice. This inhibitory effect of DABS on the tumor volume corresponds with a significant reduction of the weight of the extracted tumor when treatment ended in the group treated with DABS (FIG. 8B).

The 2,5-dihydroxybenzene sulfonate esters described in the present invention are not just prodrugs to finally administer 2,5-dihydroxybenzene sulfonate. The following examples show that these compounds in a completely unexpected manner, have by themselves pharmacological actions of interest in the invention without needing to be converted into 2,5-dihydroxybenzene sulfonate.

Example 8

Inhibition of the Mitogenesis of Fibroblasts Induced by the Fibroblast Growth Factor-1 (FGF-1)

The inhibition of mitogenesis induced by FGF-1 in quiescent cultures of Balb/c 3T3 fibroblasts by 2-acetoxy-5-hydroxybenzene sulfonate (FIG. 9), 5-acetoxy-2-hydroxybenzene sulfonate (FIG. 10) and 2,5-diacetoxybenzene sulfonate (FIG. 11) was observed. The evaluated compounds were used in the form of potassium salt, except in the first case which used calcium salt. The experiments were carried out as described in Femandez-Tomero C et al. *J Biol Chern*, 2003.

Example 9

Effect of 2,5-Dihydroxybenzene Sulfonate Monoesters on Rat C6 Glioma Cell Proliferation The following example shows the efficacy of 2,5-dihydroxybenzene sulfonic, potassium 2-acetoxy-5-hydroxybenzene sulfonate (2A-5HBS) and potassium 5-acetoxy-2-hydroxybenzene sulfonate (5A-2HBS) monoesters to reduce the proliferative capacity of glioma cells and supports the use of the compound in treating gliomas.

The cell line used was the C6 cell line and the experiment was carried out as described in examples 2 and 3. Once adhered, the cells were treated or not (controls) with (5A-2HBS) (500 µM) or (2A-5HBS) (500 µM) and they were allowed to proliferate for 48 h. After this time the glioma cell proliferation was evaluated by means of staining the fixed cells with crystal violet. The number of cells is proportional to the amount of retained dye, which was determined spectrophotometrically by measuring the absorbance at 595 nm once the dye was extracted from the cells.

Both 2,5-dihydroxybenzene sulfonate, (5A-2HBS) and (2A-5HBS) monoesters caused the inhibition of rat glioma cell proliferation (FIG. 12).

Example 10

Analysis of the Structural Interaction of 2,5-Dihydroxybenzene Sulfonate Esters with the Fibroblast Growth Factor-1 (FGF-1)

Based on the crystal diffraction of the FGF-1: 2-acetoxy-5-hydroxybenzene sulfonic acid, FGF-1: 5-acetoxy-2-hydroxybenzene sulfonic acid and FGF-1: 2,5-diacetoxybenzene sulfonic acid complexes, the structures of the complexes were calculated and represented. FIGS. 13, 14 and 15, which show the surface of the dyed protein according to its electrostatic potential (light grey, negative charge; dark grey, positive charge; white, regions with no charge), show the manner in which 2-acetoxy-5-hydroxybenzene sulfonic acid, 5-acetoxy-2-hydroxybenzene sulfonic acid and 2,5-diacetoxybenzene sulfonic acid interact, respectively, with FGF-1. The electron density of the compound, contoured at $1\sigma$ (FIGS. 13-15, panels C), allowed locating and determining the orientations of the compounds with respect to the protein (FIGS. 13-15, panels A and B), as well as confirming that the compounds conserve the acetoxyl groups in positions 2,5 and, 2 and 5, respectively, when they bind to the protein. The compounds occupy a site that is very close to the one that has been described occupied by 2,5-dihydroxybenzene sulfonic acid, the aromatic ring of which forms a cation-π bond with the NE group of lysine 132, which is marked in FIGS. 13-15, panels A, as a reference.

Each patent, patent application, and publication cited or described in the present application is hereby incorporated by reference in its entirety as if each individual patent, patent application, or publication was specifically and individually indicated to be incorporated by reference.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

What is claimed is:

1. A method for therapeutic treatment of existing basal cell carcinoma (BCC), comprising administering to a subject in need thereof, an effective amount of a pharmaceutically acceptable salt of 2,5-dihydroxybenzene derivative selected from: 2-(acetyloxy)-5-hydroxybenzenesulfonic acid, 5-(acetyloxy)-2-hydroxy benzene sulfonic acid and 2,5-bis(acety-loxy)benzenesulfonic acid.

2. The method of claim 1, wherein the pharmaceutically acceptable salt is selected from an addition salt of a mineral acid selected from hydrochloride, hydrobromide, hydroiodide, sulfate, nitrate, or phosphate; an addition salt of an organic acid selected from acetate, maleate, fumarate, citrate, oxalate, succinate, tartrate, malate, mandelate, methanesulfonate, or p-toluenesulfonate; an alkali addition salt of ammonium; a salt of an organic alkaline selected from N,N-dialkylenethanolamine, triethanolamine, glutamine, or basic amino acid salts; and a salt of a metal selected from sodium, potassium, calcium, magnesium, aluminum, or lithium.

3. The method of claim 2, wherein the pharmaceutically acceptable salt is a potassium salt.

4. The method of claim 1, wherein the pharmaceutically acceptable salt is administered topically.

5. The method of claim 1, wherein the pharmaceutically acceptable salt is administered orally, buccally, transdermally, by inhalation, rectally, intravaginally, intraocularly, or otically.

6. The method of claim 1, further comprising administration of at least one additional therapeutic agent.

7. The method of claim 6, wherein the at least one additional therapeutic agent is selected from the group consisting of: imiquimod, diclofenac, glycidic acid, trichloroacetic acid, colchicine, T4 endonuclease, 5-fluorouracil, isotretinoin, acitretin, cidofoir, 5-aminolevulinic acid, methyl aminolevulinate, hypericin, a chemotherapeutic agent, a corticosteroid, an antibiotic, an analgesic, an immunomodulator, an anti-angiogenic, a leukotriene modifier, an aminosalicylate, an anesthetic, a non-steroidal anti-inflammatory, a modifier of a solubilized interleukin receptor, a cytotoxic agent, an inhibitor of a tyrosine-kinase receptor, a protein kinase C inhibitor, and a combination of two or more thereof.

8. The method of claim 1, further comprising at least one coadjuvant therapy selected from the group consisting of: photodynamic therapy, cryotherapy, curettage, and surgery.

9. The method of claim 1, wherein the pharmaceutically acceptable salt is administered at least once per week.

10. The method of claim 8, wherein the pharmaceutically acceptable salt is administered at least once per day.

11. The method of claim 9, wherein the pharmaceutically acceptable salt is administered at least twice per day.

12. The method of claim 1, wherein the pharmaceutically acceptable salt is present in a pharmaceutical composition in an amount of about 1% w/w to about 15% w/w.

13. The method of claim 1, wherein the pharmaceutically acceptable salt is administered over a period of at least about one week.

14. The method of claim 12, wherein the pharmaceutically acceptable salt is administered over a period of at least about four weeks.

15. A method for therapeutic treatment of existing basal cell carcinoma (BCC), comprising administering to a subject in need thereof, a pharmaceutical composition comprising about 1% w/w to about 15% w/w of a potassium salt of a 2,5-dihydroxybenzene derivative selected from: 2-(acetyloxy)-5-hydroxybenzenesulfonic acid, 5-(acetyloxy)-2-hydroxy benzene sulfonic acid, and 2,5-bis(acety-loxy)benzenesulfonic acid, wherein the pharmaceutical composition is in the form of a cream administered topically at least once per day for a period of at least about one week.

* * * * *